United States Patent
Sirhan et al.

(10) Patent No.: US 7,083,642 B2
(45) Date of Patent: Aug. 1, 2006

(54) DELIVERY OF THERAPEUTIC CAPABLE AGENTS

(75) Inventors: Motasim Sirhan, Sunnyvale, CA (US); John Yan, Los Gatos, CA (US)

(73) Assignee: Avantec Vascular Corporation, Sunnyvale, CA (US)

( * ) Notice: Subject to any disclaimer, the term of this patent is extended or adjusted under 35 U.S.C. 154(b) by 20 days.

(21) Appl. No.: 10/206,853

(22) Filed: Jul. 25, 2002

(65) Prior Publication Data

US 2003/0139801 A1    Jul. 24, 2003

Related U.S. Application Data

(63) Continuation-in-part of application No. 10/002,595, filed on Nov. 1, 2001, and a continuation-in-part of application No. 09/783,253, filed on Feb. 13, 2001, now Pat. No. 6,939,375, and a continuation-in-part of application No. 09/782,927, filed on Feb. 13, 2001, now Pat. No. 6,471,980, and a continuation-in-part of application No. 09/783,254, filed on Feb. 13, 2001, and a continuation-in-part of application No. 09/782, 804, filed on Feb. 13, 2001, application No. 10/206, 853, which is a continuation-in-part of application No. 10/017,500, filed on Dec. 14, 2001.

(60) Provisional application No. 60/370,703, filed on Apr. 6, 2002, provisional application No. 60/355,317, filed on Feb. 7, 2002, provisional application No. 60/347, 473, filed on Jan. 10, 2002, provisional application No. 60/308,381, filed on Jul. 26, 2001, provisional application No. 60/258,024, filed on Dec. 22, 2000.

(51) Int. Cl.
*A61F 2/06* (2006.01)

(52) U.S. Cl. .................. 623/1.42; 623/1.15

(58) Field of Classification Search ...... 623/1.39–1.48, 623/23.29, 23.3
See application file for complete search history.

(56) References Cited

U.S. PATENT DOCUMENTS

| | | |
|---|---|---|
| 3,705,894 A | 12/1972 | Gerzon et al. |
| 3,705,946 A | 12/1972 | Dyke et al. |
| 3,777,020 A | 12/1973 | Johnson |
| 3,868,454 A | 2/1975 | Johnson |
| 3,880,995 A | 4/1975 | Jones |
| 3,903,071 A | 9/1975 | Holmes |
| 3,976,071 A | 8/1976 | Sadek |
| 3,993,749 A | 11/1976 | Sehgal et al. |
| 4,115,197 A | 9/1978 | Queener et al. |
| 4,234,684 A | 11/1980 | Abbott et al. |
| 4,335,094 A | 6/1982 | Mosbach |

(Continued)

FOREIGN PATENT DOCUMENTS

EP    063 365 B1    9/1985

(Continued)

OTHER PUBLICATIONS

Rajasubramanian et al., "Fabrication of resorbable microporus intravascular stents for gene therapy applications," *ASAIO Journal*, 40:M584-589 (1994).

(Continued)

*Primary Examiner*—Thomas Barrett
*Assistant Examiner*—David A. Izquierdo
(74) *Attorney, Agent, or Firm*—Townsend and Townsend and Crew LLP

(57) ABSTRACT

The present invention provides improved stents and other prostheses for delivering substances to vascular and other luminal and intracorporeal environments. In particular, the present invention provides for therapeutic capable agent eluting stents with minimized undesirable loss of the therapeutic capable agent during expansion of the stent.

14 Claims, 14 Drawing Sheets

U.S. PATENT DOCUMENTS

| | | | |
|---|---|---|---|
| 4,345,588 A | 8/1982 | Widder et al. | |
| 4,357,259 A | 11/1982 | Wenyel et al. | |
| 4,501,726 A | 2/1985 | Schröder et al. | |
| 4,810,524 A | 3/1989 | Nakayama et al. | |
| 4,832,686 A | 5/1989 | Anderson | |
| 4,871,716 A | 10/1989 | Longo et al. | |
| 4,883,666 A | 11/1989 | Sabel et al. | |
| 4,894,231 A | 1/1990 | Moreau et al. | |
| 4,897,268 A | 1/1990 | Tice et al. | |
| 4,904,479 A | 2/1990 | Illum | |
| 4,921,723 A | 5/1990 | Nichols et al. | |
| 4,936,281 A | 6/1990 | Stasz | |
| 5,000,185 A | 3/1991 | Yock | |
| 5,024,671 A | 6/1991 | Tu et al. | |
| 5,067,491 A | 11/1991 | Taylor, II et al. | |
| 5,069,216 A | 12/1991 | Groman et al. | |
| 5,112,457 A | 5/1992 | Marchant | |
| 5,163,952 A | 11/1992 | Froix | |
| 5,171,264 A * | 12/1992 | Merrill | 623/3.1 |
| 5,176,907 A | 1/1993 | Leong | |
| 5,206,159 A | 4/1993 | Cohen et al. | |
| 5,225,282 A | 7/1993 | Chagnon et al. | |
| 5,283,257 A | 2/1994 | Gregory et al. | |
| 5,286,254 A | 2/1994 | Shapland et al. | |
| 5,342,348 A | 8/1994 | Kaplan | |
| 5,355,832 A | 10/1994 | Loh et al. | |
| 5,356,433 A | 10/1994 | Rowland et al. | |
| 5,368,557 A | 11/1994 | Nita et al. | |
| 5,409,000 A | 4/1995 | Imran | |
| 5,411,550 A | 5/1995 | Herweck et al. | |
| 5,419,760 A | 5/1995 | Narciso, Jr. | |
| 5,447,724 A | 9/1995 | Helmus et al. | |
| 5,447,799 A | 9/1995 | Loh et al. | |
| 5,463,010 A | 10/1995 | Hu et al. | |
| 5,464,450 A | 11/1995 | Buscemi et al. | |
| 5,464,650 A | 11/1995 | Berg et al. | |
| 5,474,563 A | 12/1995 | Myler et al. | |
| 5,484,584 A | 1/1996 | Wallace et al. | |
| 5,500,013 A | 3/1996 | Buscemi et al. | |
| 5,512,055 A * | 4/1996 | Domb et al. | 604/265 |
| 5,516,781 A | 5/1996 | Morris et al. | |
| 5,543,158 A | 8/1996 | Gref et al. | |
| 5,545,208 A | 8/1996 | Wolff et al. | |
| 5,551,954 A | 9/1996 | Buscemi et al. | |
| 5,563,146 A | 10/1996 | Morris et al. | |
| 5,569,463 A | 10/1996 | Helmus et al. | |
| 5,591,227 A | 1/1997 | Dinh et al. | |
| 5,609,629 A | 3/1997 | Fearnot et al. | |
| 5,624,411 A | 4/1997 | Tuch | |
| 5,637,113 A | 6/1997 | Tartaglia et al. | |
| 5,646,160 A | 7/1997 | Morris et al. | |
| 5,649,977 A | 7/1997 | Campbell | |
| 5,656,297 A | 8/1997 | Bernstein et al. | |
| 5,665,728 A | 9/1997 | Morris et al. | |
| 5,679,400 A | 10/1997 | Tuch | |
| 5,700,286 A | 12/1997 | Tartaglia et al. | |
| 5,725,494 A | 3/1998 | Brisken | |
| 5,725,567 A | 3/1998 | Wolff et al. | |
| 5,728,062 A | 3/1998 | Brisken | |
| 5,735,811 A | 4/1998 | Brisken | |
| 5,769,883 A | 6/1998 | Buscemi et al. | |
| 5,769,884 A | 6/1998 | Solovay | |
| 5,824,049 A | 10/1998 | Ragheb et al. | |
| 5,837,008 A | 11/1998 | Berg et al. | |
| 5,843,172 A | 12/1998 | Yan | |
| 5,851,231 A | 12/1998 | Wolff et al. | |
| 5,866,113 A * | 2/1999 | Hendriks et al. | 424/78.17 |
| 5,876,452 A | 3/1999 | Athanasiou et al. | |
| 5,879,808 A | 3/1999 | Wary et al. | |
| 5,891,108 A | 4/1999 | Leone et al. | |
| 5,893,840 A | 4/1999 | Hull et al. | |
| 5,928,145 A | 7/1999 | Ocali et al. | |
| 5,951,586 A | 9/1999 | Berg et al. | |
| 5,958,510 A | 9/1999 | Sivaramakrishnam et al. | |
| 5,968,092 A | 10/1999 | Buscemi et al. | |
| 5,972,027 A | 10/1999 | Johnson | |
| 5,980,551 A | 11/1999 | Summers et al. | |
| 5,980,566 A | 11/1999 | Alt et al. | |
| 5,997,468 A | 12/1999 | Wolff et al. | |
| 6,031,375 A | 2/2000 | Atalar et al. | |
| 6,051,276 A | 4/2000 | Wary et al. | |
| 6,054,122 A | 4/2000 | MacPhee | |
| 6,063,101 A | 5/2000 | Jacobsen et al. | |
| 6,069,295 A * | 5/2000 | Leitao | 623/11.11 |
| 6,071,305 A | 6/2000 | Brown et al. | |
| 6,086,952 A | 7/2000 | Lang et al. | |
| 6,096,070 A | 8/2000 | Ragheb et al. | |
| 6,099,561 A | 8/2000 | Alt | |
| 6,107,052 A | 8/2000 | Dorn | |
| 6,153,252 A | 11/2000 | Hossainy et al. | |
| 6,183,507 B1 | 2/2001 | Lashinski et al. | |
| 6,197,013 B1 | 3/2001 | Reed et al. | |
| 6,203,536 B1 | 3/2001 | Berg et al. | |
| 6,214,901 B1 | 4/2001 | Chudzik et al. | |
| 6,240,616 B1 | 6/2001 | Yan | |
| 6,253,443 B1 | 7/2001 | Johnson | |
| 6,273,908 B1 | 8/2001 | Ndondo-Lay | |
| 6,273,913 B1 | 8/2001 | Wright et al. | |
| 6,287,628 B1 | 9/2001 | Hossainy et al. | |
| 6,299,604 B1 | 10/2001 | Ragheb et al. | |
| 6,344,035 B1 | 2/2002 | Chudzik et al. | |
| 6,395,326 B1 | 5/2002 | Castro et al. | |
| 6,471,980 B1 | 10/2002 | Sirhan et al. | |
| 6,585,765 B1 * | 7/2003 | Hossainy et al. | 623/1.45 |
| 6,613,082 B1 * | 9/2003 | Yang | 623/1.42 |
| 6,663,662 B1 * | 12/2003 | Pacetti et al. | 623/1.13 |
| 2001/0027340 A1 | 10/2001 | Wright et al. | |
| 2001/0029351 A1 | 10/2001 | Falotico et al. | |
| 2002/0005206 A1 | 1/2002 | Falotico et al. | |
| 2002/0007213 A1 | 1/2002 | Falotico et al. | |
| 2002/0007214 A1 | 1/2002 | Falotico | |
| 2002/0007215 A1 | 1/2002 | Falotico et al. | |
| 2002/0016625 A1 | 2/2002 | Falotico et al. | |
| 2002/0032414 A1 | 3/2002 | Ragheb et al. | |

FOREIGN PATENT DOCUMENTS

| | | |
|---|---|---|
| EP | 184 162 B1 | 4/1994 |
| EP | 0 923 953 A2 | 6/1999 |
| EP | 0950386 A2 | 10/1999 |
| EP | 0950386 A3 | 10/1999 |
| EP | 1277449 A | 1/2003 |
| WO | WO 90/13332 | 11/1990 |
| WO | WO 98/36784 A1 | 8/1998 |
| WO | WO 00/10622 A1 | 3/2000 |
| WO | WO 01/01957 | 1/2001 |
| WO | WO 01/41678 | 6/2001 |
| WO | WO 02/083039 | 10/2002 |

OTHER PUBLICATIONS

U.S. Appl. No. 09/782,927, filed Feb. 13, 2001, entitled "Intravascular delivery of mycophenolic acid."

U.S. Appl. No. 09/783,254, filed Feb. 13, 2001, entitled Intravascular delivery of mizorbine.

U.S. Appl. No. 09/782,804, filed Feb. 13, 2001, entitled Intravascular delivery of methylprednisolone.

Mohacsi et al., "Different inhibitory effects of immunosuppresive drugs on hyman and rat aortic smooth muscle and endothelial cell proliferation stimulated by platelet-derived growth factor or endothelial cell growth factor" *J Heart and Lung Transplant*, 16:484-491 (1997).

Nghiem, et al.; "Tacrolimus and Pimecrolimus: From Clever Prokaryotes to Inhibiting Calcineurin and Treating Atopic Dermatitis;" *J Am Acad Dermatol*; Feb. 2002; pp. 228-241; vol. 46; No. 2; American Academy of Deratology, Inc.

Web page; "Ascomycin Macrolactams;" Ascomycin Macrolactams Fact Sheet; at URL=http://ascomycin.noneto.com/; printed Mar. 11, 2004; 2 pages.

* cited by examiner

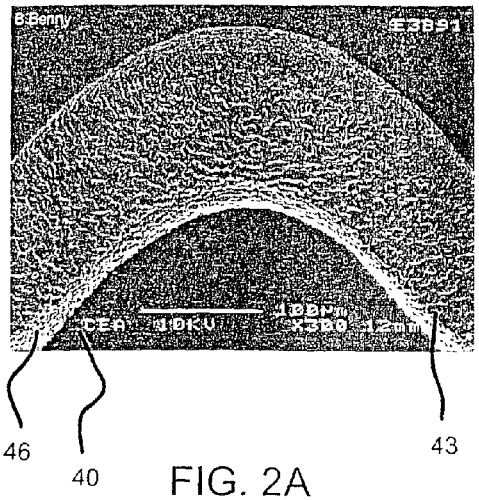
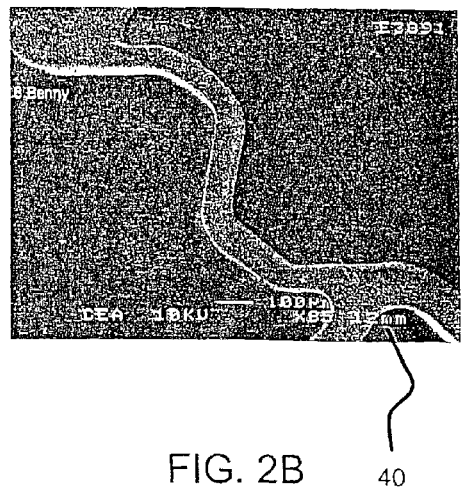
FIG. 2A    FIG. 2B
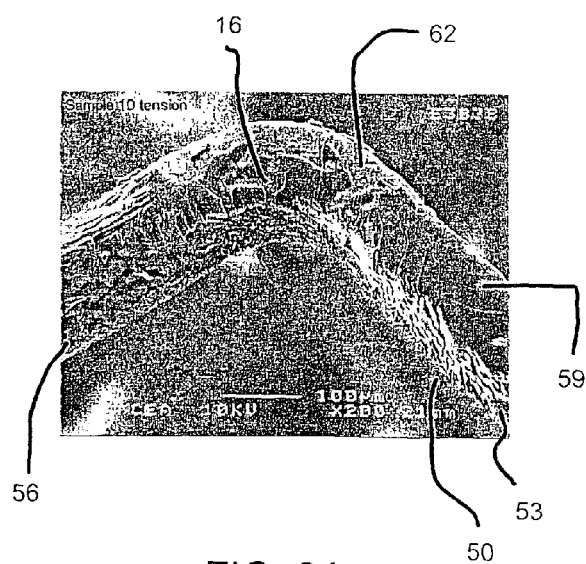
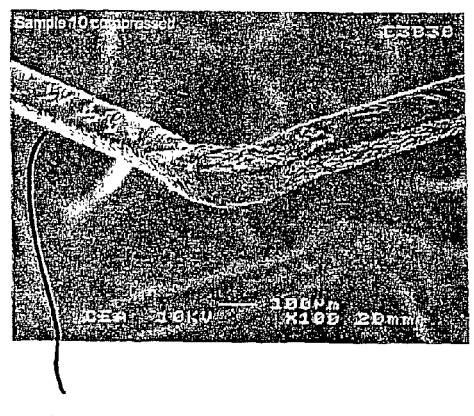
FIG. 3A    FIG. 3B

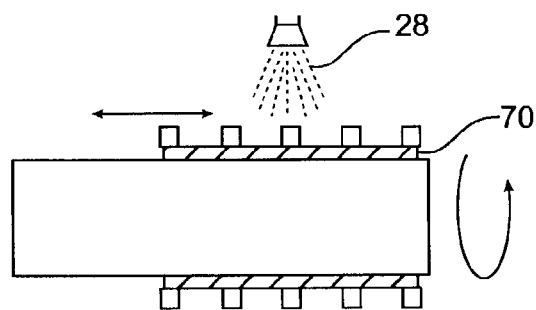
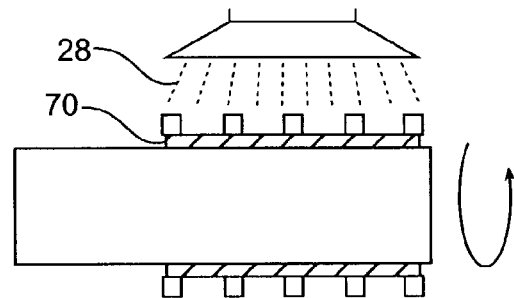
FIG. 9A
FIG. 9B
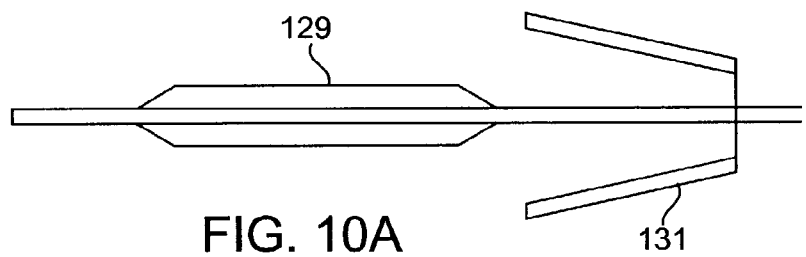
FIG. 10A
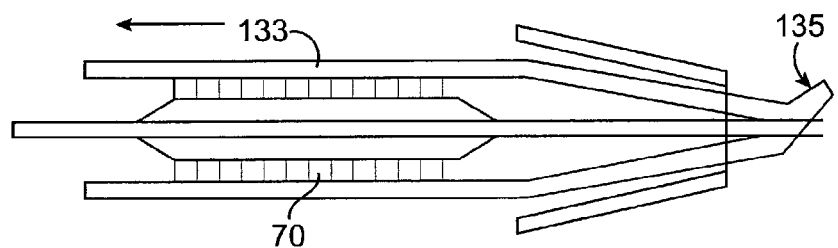
FIG. 10B

DELIVERY OF THERAPEUTIC CAPABLE AGENTS

CROSS-REFERENCES TO RELATED APPLICATIONS

This application claims the benefit of priority from U.S. Provisional Patent Application No. 60/370,703, filed on Apr. 6, 2002, No. 60/355,317, filed Feb. 7, 2002, and No. 60/347,473, filed on Jan. 10, 2002; and is a continuation-in-part of U.S. Patent Application Ser. No. 10/002,595, filed on Nov. 1, 2001, which claims the benefit of priority from U.S. Provisional Patent Application Ser. No. 60/308,381, filed on Jul. 26, 2001, and is a continuation-in-part of U.S. patent application Ser. No. 09/783,253 now U.S. Pat. No. 6,939,375, U.S. patent application Ser. No. 09/782,927 now U.S. Pat. No. 6,471,980, and U.S. patent application Ser. Nos. 09/783,254, 09/782,804 all of which were filed on Feb. 13, 2001 and claim the benefit of priority from U.S. Provisional Patent Application No. 60/258,024, filed on Dec. 22, 2000; and is a continuation-in-part of U.S. patent application Ser. No. 10/017,500, filed on Dec. 14, 2001. Each of the above applications is assigned to the assignee of the present application, the full disclosure of each which is incorporated herein by reference in its entirety. The disclosure of this present application is also related to the disclosures of U.S. patent application Ser. Nos. 10/206,807, and 10/206,803, both filed concurrently herewith, and assigned to the same assignee as that of the present application, the full disclosures of which are incorporated herein by reference in their entirety.

FIELD OF INVENTION

The present invention relates generally to medical devices and methods. More particularly, the present invention relates to luminal prostheses, such as vascular stents and grafts for inhibiting restenosis and hyperplasia.

BACKGROUND OF THE INVENTION

A number of percutaneous intravascular procedures have been developed for treating stenotic atherosclerotic regions of a patient's vasculature to restore adequate blood flow. The most successful of these treatments is percutaneous transluminal angioplasty (PTA). In PTA, a catheter, having an expandable distal end usually in the form of an inflatable balloon, is positioned in the blood vessel at the stenotic site. The expandable end is expanded to dilate the vessel to restore adequate blood flow beyond the diseased region. Other procedures for opening stenotic regions include directional arthrectomy, rotational arthrectomy, laser angioplasty, stenting, and the like. While these procedures have gained wide acceptance (either alone or in combination, particularly PTA in combination with stenting), they continue to suffer from significant disadvantages. A particularly common disadvantage with PTA and other known procedures for opening stenotic regions is the frequent occurrence of restenosis.

Restenosis refers to the re-narrowing of an artery after an initially successful angioplasty. Restenosis afflicts approximately up to 50% of all angioplasty patients and is the result of injury to the blood vessel wall during the lumen opening angioplasty procedure. In some patients, the injury initiates a repair response that is characterized by smooth muscle cell proliferation referred to as "hyperplasia" in the region traumatized by the angioplasty. This proliferation of smooth muscle cells re-narrows the lumen that was opened by the angioplasty within a few weeks to a few months, thereby necessitating a repeat PTA or other procedure to alleviate the restenosis.

A number of strategies have been proposed to treat hyperplasia and reduce restenosis. Previously proposed strategies include prolonged balloon inflation during angioplasty, treatment of the blood vessel with a heated balloon, treatment of the blood vessel with radiation following angioplasty, stenting of the region, and other procedures. While these proposals have enjoyed varying levels of success, no one of these procedures is proven to be entirely successful in substantially or completely avoiding all occurrences of restenosis and hyperplasia.

As an alternative or adjunctive to the above mentioned therapies, the administration of therapeutic agents following PTA for the inhibition of restenosis has also been proposed. Therapeutic treatments usually entail pushing or releasing a drug through a catheter or from a stent. While holding great promise, the delivery of therapeutic agents for the inhibition of restenosis has not been entirely successful.

Accordingly, it would be a significant advance to provide improved devices and methods for inhibiting restenosis and hyperplasia concurrently with and/or following angioplasty and other interventional treatments. This invention satisfies at least some of these and other needs.

BRIEF SUMMARY OF THE INVENTION

The present invention provides improved devices and methods for inhibiting stenosis, restenosis, or hyperplasia concurrently with and/or after intravascular intervention. As used herein, the term "inhibiting" means any one of reducing, treating, minimizing, containing, preventing, curbing, eliminating, holding back, or restraining. In particular, the present invention provides luminal prostheses which allow for programmed and controlled substance delivery with increased efficiency and/or efficacy to selected locations within a patient's vasculature to inhibit restenosis. Moreover, the present invention minimizes drug washout and provides minimal to no hindrance to endothelialization of the vessel wall.

The present invention is directed to improved devices and methods for preparation or treatment of susceptible tissue sites. As used herein, "susceptible tissue site" refers to a tissue site that is injured, or may become injured as a result of an impairment (e.g., disease, medical condition), or may become injured during or following an interventional procedure such as an intravascular intervention. The term "intravascular intervention" includes a variety of corrective procedures that may be performed to at least partially resolve a stenotic, restenotic, or thrombotic condition in a blood vessel, usually an artery, such as a coronary artery. Usually, the corrective procedure will comprise balloon angioplasty. The corrective procedure may also comprise directional atherectomy, rotational atherectomy, laser angioplasty, stenting, or the like, where the lumen of the treated blood vessel is enlarged to at least partially alleviate a stenotic condition which existed prior to the treatment. The susceptible tissue site may include tissues associated with intracorporeal lumens, organs, or localized tumors. In one embodiment, the present devices and methods reduce the formation or progression of restenosis and/or hyperplasia which may follow an intravascular intervention. In particular, the present invention is directed to corporeal, in particular intracorporeal devices and methods using the same.

As used herein, the term "intracorporeal body" refers to body lumens or internal corporeal tissues and organs, within a corporeal body. The "body lumen" may be any blood vessel in the patient's vasculature, including veins, arteries, aorta, and particularly including coronary and peripheral arteries, as well as previously implanted grafts, shunts, fistulas, and the like. It will be appreciated that the present invention may also be applied to other body lumens, such as the biliary duct, which are subject to excessive neoplastic cell growth. Examples of internal corporeal tissue and organ applications include various organs, nerves, glands, ducts, and the like. In one embodiment, the device includes luminal prostheses such as vascular stents or grafts. In another embodiment, the device may include cardiac pacemaker leads or lead tips, cardiac defibrillator leads or lead tips, heart valves, sutures, needles, pacemakers, orthopedic devices, appliances, implants or replacements, or portions of any of the above.

In one embodiment of the present invention, a luminal delivery prosthesis comprises a scaffold which is implantable in a body lumen and means on the scaffold for releasing a substance. The scaffold may be in the form of a stent, which additionally maintains luminal patency, or may be in the form of a graft, which additionally protects or enhances the strength of a luminal wall. The scaffold may be radially expansible and/or self-expanding and is preferably suitable for luminal placement in a body lumen. An exemplary stent for use in the present invention is described in co-pending U.S. patent application Ser. No. 09/565,560, assigned to the assignee of the present application, the full disclosure of which is incorporated herein by reference.

In one embodiment, the devices and methods of the present invention inhibit the occurrence of restenosis while allowing for the generation of small amount of cellularization, endothelialization, or neointima, preferably, in a controlled manner. "Restenosis" in this instance is defined as when the artery narrows greater than about 40% to about 80% of the acute vessel diameter achieved by the vascular intervention, such as stenting, usually from about 50% to about 70%.

In an embodiment, the device includes a structure and at least one source of at least one therapeutic capable agent associated with the structure. As used herein, the term "associated with" refers to any form of association such as directly or indirectly being coupled to, connected to, disposed on, disposed within, attached to, adhered to, bonded to, adjacent to, entrapped in, absorbed in, absorbed on, and like configurations. The therapeutic capable agent source may be associated at least in part with the structure in a manner as to become available, immediately or after a delayed period, to the susceptible tissue site upon introduction of the device within or on the corporeal body. The source may be disposed or formed adjacent at least a portion of the structure. In one embodiment, the source may be disposed or formed adjacent at least a portion of either or both surfaces of the expandable structure, within an interior of the structure disposed between the two surfaces, or any combination thereof. In one embodiment, the source may be disposed only on one of the longitudinal surfaces, namely, the tissue facing surface. The association of the therapeutic capable agent with the structure may be continuous or in discrete segments. In an embodiment, the structure may be an expandable structure. In another embodiment, the structure may have a substantially constant size or diameter, or alternatively depending on the application and use, may be a contractable structure. In an embodiment, the structure includes at least one surface, usually, a tissue facing surface (i.e., abluminal surface). In another embodiment, the structure includes an abluminal surface and another surface, usually a lumen facing surface. In an embodiment, the structure may have an interior disposed between two luminal and abluminal surfaces.

The therapeutic capable agent is associated with the structure in such a manner as to avoid or minimize unwanted loss (including, but not limited to, flaking or dislodging of the drug layer) of the therapeutic capable agent prior to the disposing of the device, such as a stent, at its intended intracorporeal location. Such therapeutic capable agent loss due to flaking is particularly undesirable for a multiple of reasons including downstream embolic effects, therapeutic capable agent release at an initial rate higher than preferred, relatively rapid exhaustion of the therapeutic capable agent, all of which could lead to potentially severe health complications.

In one embodiment, the present invention provides for therapeutic capable agent eluting devices, such as intraluminal stents, capable of delivering the therapeutic capable agent at a desired point in time after disposal of the device at its intended site without necessarily any aid from other material, such as rate limiting materials (e.g., rate limiting polymeric materials), thus minimizing the need for additional components in the design of the drug eluting stent.

In one embodiment, the therapeutic capable agent is disposed adjacent at least one of the structure (e.g., stent) surfaces, usually the abluminal surface (i.e., tissue-facing surface). In another embodiment, the therapeutic capable agent is disposed adjacent both surfaces, luminal and abluminal surfaces. The therapeutic capable agent may also be disposed on two radial edges of the stent.

In a preferred embodiment, the therapeutic capable agent is disposed adjacent the stent in such a manner as to minimize stress or strain that would typically be placed upon a therapeutic capable agent surface upon expansion of the stent within or without the corporeal body. In one embodiment, the stress upon the therapeutic capable agent surface may be reduced or minimized by preparing the therapeutic capable agent surface to include textured characteristics.

The therapeutic capable agent surface is preferably prepared to include a surface having peaks with a mean distance between adjacent peaks ranging from about 0.1 μm to about 50 μm, usually ranging from about 1 μm to about 35 μm, typically ranging from about 5 μm to about 20 μm. The peaks may have an average height (distance between the base of the peak and the apex of the peak) ranging from about 0.01 μm to about 10 μm, usually ranging from about 0.05 μm to about 1.5 μm, typically ranging from about 0.1 μm to about 1 μm. The therapeutic capable agent may be disposed to have an average thickness ranging from about 0.1 μm to about 20 μm, usually ranging from about 0.5 μm to about 7.5 μm, typically ranging from about 1 μm to about 5 μm.

In one embodiment, the stress upon the therapeutic capable agent surface may be reduced or minimized by disposing the therapeutic capable agent on areas of the stent which exhibit lower mechanical stress or strain profiles (i.e., mechanical profiles) upon expansion or contraction, or areas which are not substantially in a direct line of fluid (e.g., blood or other bodily fluids) flow through the body. The disposing of the therapeutic capable agent at the relatively lower mechanical profile areas reduces undesirable or unwanted flaking and/or premature loss.

The device may include an expandable structure implantable within a corporeal body which includes the susceptible tissue site. The device, alternatively, may be an implantable device configured for implanting at a targeted corporeal site. The targeted corporeal site may include the susceptible tissue site or may be another corporeal site (e.g., other body organs or lumens). For example, a corporeal site may comprise a targeted intracorporeal site such as an artery, which supplies blood to the susceptible tissue site. In an embodiment, the expandable structure may be in the form of a stent, which additionally maintains luminal patency, or in the form of a graft, which additionally protects or enhances the strength of a luminal wall. The device, may comprise at least in part, a scaffold formed from an open lattice or an at least substantially closed surface. In an embodiment, the stent comprises a scaffold formed at least in part from an open lattice. The expandable structure may be radially expandable and/or self-expanding and is preferably suitable for luminal placement in a body lumen.

The expandable structure may be formed of any suitable material such as metals, polymers, or a combination thereof. In an embodiment, the structure may be formed from malleable metals or alloys, such as 300 series stainless steel; resilient metals, such as superelastic and shape memory alloys (e.g., nitinol alloys, spring stainless steels, and the like); non-metallic materials, such as ceramics- or polymeric materials; or a combination thereof.

In one embodiment, the expandable structure may be formed of an at least partially biodegradable material selected from the group consisting of polymeric material, metallic materials, ceramic materials, or combinations thereof. The at least partially biodegradable material, preferably degrades over time. Examples of polymeric material include poly-L-lactic acid, having a delayed degradation to allow for the recovery of the vessel before the structure is degraded. Examples of metallic material include metals or alloys degradable in the corporeal body, such as stainless steel. Other suitable material for use as the structure include carbon or carbon fiber, cellulose acetate, cellulose nitrate, silicone, polyethylene terphthalate, polyurethane, polyamide, polyester, polyorthoester, polyanhydride, polyether sulfone, polycarbonate, polytetrafluoroethylene, another biocompatible polymeric material, polyanhydride, polycaprolactone, polyhydroxybutyrate valerate, another biodegradable polymer, protein, an extracellular matrix component, collagen, fibrin, another biologic agent, or a suitable mixture or copolymer of any of the materials listed above, degradable, non-degradable, metallic, or otherwise.

In an embodiment, the device is a stent generally including a cylindrical frame having proximal and distal ends, and tissue and luminal facing surfaces. The device usually further comprises a plurality of radially expansible unit segments including rings. The rings preferably have a serpentine shape. In an embodiment, the unit segments preferably include segments having different mechanical profiles which, for example, may be exhibited as a result of expansion. In an embodiment, some of the rings may be joined with at least one axially adjacent ring through expansion links. The links preferably have a sigmoidal shape, more preferably, an S shape having a relatively smooth profile along its length to minimize or reduce kinking upon expansion. Similarly, the links may comprise segments having different mechanical profiles along their length. For example, the unit segments and/or links may have relatively lower mechanical profile portions along their lengths with relatively higher mechanical profile portions at bends, points, intersections, joints, or areas exposed to flow turbulence.

In one embodiment, a luminal prosthesis makes available one or more therapeutic capable agents to one or more selected locations within a patient's vasculature, including the susceptible tissue site, to reduce the formation or progression of restenosis and/or hyperplasia. As used herein, the term "made available" means to have provided the substance (e.g., therapeutic capable agent) at the time of release or administration, including having made the substance available at a corporeal location such as an intracorporeal location or target site, regardless of whether the substance is in fact delivered, used by, or incorporated into the intended site, such as the susceptible tissue site.

The delivery of the therapeutic capable agent to the susceptible tissue site, or making the therapeutic capable agent available to the susceptible tissue site, may be direct or indirect through another corporeal site. In the latter embodiment, the another corporeal site is a targeted intracorporeal site, for example an intracorporeal lumen, such as an artery, supplying blood to the susceptible tissue site.

As used herein, "therapeutic capable agent" includes at least one compound, molecular species, and/or biologic agent that is either therapeutic as it is introduced to the subject under treatment, becomes therapeutic after being introduced to the subject under treatment as for example by way of reaction with a native or non-native substance or condition, or another introduced substance or condition. Examples of native conditions include pH (e.g., acidity), chemicals, temperature, salinity, osmolality, and conductivity; with non-native conditions including those such as magnetic fields, electromagnetic fields (such as radiofrequency and microwave), and ultrasound. In the present application, the "chemical name" of any of the therapeutic capable agents or other compounds is used to refer to the compound itself and to pro-drugs (precursor substances that are converted into an active form of the compound in the body), and/or pharmaceutical derivatives, analogues, or metabolites thereof (bio-active compound to which the compound converts within the body directly or upon introduction of other agents or conditions (e.g., enzymatic, chemical, energy), or environment (e.g., pH)).

The therapeutic capable agent may be selected from a group consisting of immunosuppressants, anti-inflammatories, anti-proliferatives, anti-migratory agents, anti-fibrotic agents, proapoptotics, vasodilators, calcium channel blockers, anti-neoplastics, anti-cancer agents, antibodies, anti-thrombotic agents, anti-platelet agents, IIb/IIIa agents, anti-viral agents, mTOR (mammalian target of rapamycin) inhibitors, non-immunosuppressant agents, and a combination thereof. Specific examples of therapeutic capable agent include: mycophenolic acid, mycophenolic acid derivatives (e.g., 2-methoxymethyl derivative and 2-methyl derivative), VX-148, VX-944, mycophenolate mofetil, mizoribine, methylprednisolone, dexamethasone, CERTICAN™ (e.g., everolimus, RAD), rapamycin, ABT-773 (Abbot Labs), ABT-797 (Abbot Labs), TRIPTOLIDE™, METHOTREXATE™, phenylalkylamines (e.g., verapamil), benzothiazepines (e.g., diltiazem), 1,4-dihydropyridines (e.g., benidipine, nifedipine, nicarrdipine, isradipine, felodipine, amlodipine, nilvadipine, nisoldipine, manidipine, nitrendipine, barnidipine (HYPOCA™)), ASCOMYCIN™, WORTMANNIN™, LY294002, CAMPTOTHECIN™, flavopiridol, isoquinoline, HA-1077 (1-(5-isoquinolinesulfonyl)-homopiperazine hydrochloride), TAS-301 (3-bis(4-methoxyphenyl)methylene-2-indolinone), TOPOTECAN™, hydroxyurea, TACROLIMUS™ (FK 506), cyclophosphamide, cyclosporine, daclizumab, azathioprine, prednisone, diferuloymethane, diferuloylmethane, diferulylmethane, GEMCITABINE™, cilostazol (PLETAL™), tranilast, enalapril, quercetin, suramin, estradiol, cycloheximide, tiazofurin, zafurin, AP23573, rapamycin derivatives, non-immunosuppressive analogues of rapamycin (e.g., rapalog, AP21967, derivatives' of rapalog), CCI-779 (an analogue of rapamycin available from Wyeth), sodium mycophernolic acid, benidipine hydrochloride, sirolimus, rapamine, metabolites, derivatives, and/or combinations thereof.

The devices of the present invention may be configured to release or make available the therapeutic capable agent at one or more phases, the one or more phases having similar or different performance (e.g., release) profiles. The therapeutic capable agent may be made available to the tissue at amounts which may be sustainable, intermittent, or continuous; in one or more phases and/or rates of delivery; effective to reduce any one or more of smooth muscle cell proliferation, inflammation, immune response, hypertension, or those complementing the activation of the same. Any one of the at least one therapeutic capable agents may perform one or more functions, including preventing or reducing proliferative/restenotic activity, reducing or inhibiting thrombus formation, reducing or inhibiting platelet activation, reducing or preventing vasospasm, or the like.

The total amount of therapeutic capable agent made available to the tissue depends in part on the level and amount of desired therapeutic result. The therapeutic capable agent may be made available at one or more phases, each phase having similar or different release rate and duration as the other phases. The release rate may be pre-defined. In an embodiment, the rate of release may provide a sustainable level of therapeutic capable agent to the susceptible tissue site. In another embodiment, the rate of release is substantially constant. The rate may decrease and/or increase over time, and it may optionally include a substantially non-release period. The release rate may comprise a plurality of rates. In an embodiment the plurality of release rates include at least two rates selected from the group consisting of substantially constant, decreasing, increasing, substantially non-releasing.

The total amount of therapeutic capable agent made available or released may be in an amount ranging from about 0.1 µg (micrograms) to about 10 g (grams), generally about 0.1 µg to about 10 mg (milligrams), usually from about 1 µg to about 10 mg, from 1 µg to about 5 mg, from about 1 µg to about 2 mg, from 10 fig to about 2 mg, from 10 µg to about 1 mg, from about 50 µg to about 1 mg, or from 50 fig to about 500 µg. In an embodiment, the therapeutic capable agent may be released in a time period, as measured from the time of implanting of the device, ranging from about 1 day to about 200 days; from about 1 day to about 45 days; or from about 7 days to about 21 days. In an embodiment the release rate of the therapeutic capable agent per day may range from about 0.001 µg to about 500 µg, from about 0.001 µg to about 200 µg, from about 0.5 µg to about 200 µg, usually, from about 1.0 µg to about 100 µg, from about 1 µg to about 60 µg, and typically, from about 5 µg to about 50 µg.

The therapeutic capable agent may be made available at an initial phase and one or more subsequent phases. When the therapeutic capable agent is delivered at different phases, the initial delivery rate will typically be from about 0 to about 99% of the subsequent release rates, usually from about 0% to about 90%, preferably from about 0% to 75%, more preferably from about 0% to 50%. The rate of delivery during the initial phase will typically range from about 0.001 ng per day to about 500 µg per day, from about 0 to about 50 µg per day, usually from about 0.001 ng (nanograms) per day to about 50 µg per day, more usually from about 0.1 µg per day to about 30 µg per day, more preferably, from about 1 µg per day to about 20 µg per day. The rate of delivery at the subsequent phase may range from about 0.01 ng per day to about 500 µg per day, from about 0.01 µg per day to about 200 µg per day, usually from about 1 µg per day to about 100 µg per day. In one embodiment, the therapeutic capable agent is made available to the susceptible tissue site in a programmed and/or controlled manner with increased efficiency and/or efficacy. Moreover, the present invention provides limited or reduced hindrance to endothelialization of the vessel wall.

The duration of the initial, subsequent, and any other additional phases may vary. For example, the release of the therapeutic capable agent may be delayed from the initial implantation of the device. Typically, the delay is sufficiently long to allow the generation of sufficient cellularization or endothelialization at the treated site to inhibit loss of the therapeutic capable agent into the vascular lumen. Typically, the duration of the initial phase will be sufficiently long to allow initial cellularization or endothelialization-of at least part of the device. Typically, the duration of the initial phase, whether being a delayed phase or a release phase, is less than about 24 weeks, from about 1 hour to about 24 weeks, usually less than about 12 weeks, more usually from about 1 hour to about 8 weeks, from about 1 day to about 30 days, from about 12 hours to about 4 weeks, from about 12 hours to about 2 weeks, from about 1 day to about 2 weeks, or from about 1 day to about 1 week.

The durations of the one or more subsequent phases may also vary, typically being from about 4 hours to about 24 weeks, from about 1 hour to about 12 weeks, from about 1 day to about 12 weeks, from about 1 hour to about 8 weeks, from about 4 hours to about 8 weeks, from about 2 days to about 8 weeks, from about 2 days to about 45 days, more preferably from about of 3 days to about 50 days, from about 3 days to about 30 days, most preferably from about 1 hour to about 1 day. In an embodiment, the duration specified relates to a vascular environment. The more than one phase may include similar or different durations, amounts, and/or rates of release. For example, in one scenario, there may be an initial phase of delay, followed by a subsequent phase of release at a first subsequent rate, and a second subsequent phase of release at a second subsequent rate, and the like.

In an embodiment a mammalian tissue concentration of the substance at an initial phase will typically be within a range from about 0.001 ng/mg of tissue to about 100 µg/mg of tissue; from about 1 ng/mg of tissue to about 100 µg/mg of tissue; from about 10 ng/mg of tissue to about 100 µg/mg of tissue; from about 0.1 ng/mg of tissue to about 50 µg/mg of tissue; from about 1 ng/mg of tissue to about 10 µg/mg of tissue; from about 1 ng/mg of tissue to about 1 µg/mg of tissue. A mammalian tissue concentration of the substance at a subsequent phase will typically be within a range from about 0.001 ng/mg of tissue to about 600 µg/mg of tissue, preferably from about 0.001 ng/mg of tissue to about 100 µg/mg of tissue, from about 0.1 ng/mg of tissue to about 10 µg/mg of tissue, from about 1 ng/mg of tissue to about 10 µg/mg of tissue.

The source may be associated with at least a portion of the structure (e.g., prosthesis) using coating methods such as spraying, dipping, deposition (vapor or plasma), painting, and chemical bonding. Such coatings may be uniformly or intermittently applied to the structure or may be applied in a random or pre-determined pattern. In an embodiment, when the structure includes one or more surfaces and optional interior between the surfaces, the coating may be applied to only one of the surfaces of the prosthesis or the coating may be thicker on one side.

When the device includes the source including a plurality of compounds (e.g., first therapeutic capable agent and an another compound such as another or second therapeutic capable agent or enabling compound), the plurality of compounds may be released at different times and/or rates, from the same or different layers. Each of the plurality of compounds may be made available independently of one another (e.g., sequential), simultaneous with one another, or concurrently with and/or subsequent to the interventional procedure. For example, a first therapeutic capable agent (e.g., TRIPTOLIDE™) may be released within a time period of 1 day to 45 days with the second therapeutic capable agent (e.g, mycophenolic acid) released within a time period of 2 days to 3 months, from the time of interventional procedure.

The devices of the present invention may be provided together with instructions for use (IFU), separately or as part of a kit. The kit may include a pouch or any other suitable package, such as a tray, box, tube, or the like, to contain the device and the IFU, where the IFU may be printed on a separate sheet or other media of communication and/or on the packaging itself. In an embodiment, the kit may also include a mounting hook such as a crimping device and/or an expansible inflation member which may be permanently or releaseably coupled to the device of the present invention.

In operation, methods of delivering the therapeutic capable agents to the susceptible tissue site comprise positioning the source of the therapeutic capable agent within the intracorporeal site, such as the vascular lumen. The therapeutic capable agent is released and/or made available to the susceptible tissue site. In an embodiment, the releasing of the therapeutic capable agent occurs at a pre-determined time period following the positioning of the source. The delay in the release of the therapeutic capable agent may be for a sufficiently long period of time to allow sufficient generation of intimal tissue to reduce the occurrence of a thrombotic event. The device may comprise a rate-controlling element. In an embodiment, the source includes the rate-controlling element. In one embodiment, the releasing of the therapeutic capable agent may occur by surface degradation or hydrolysis of the source. In yet another embodiment, the release of the therapeutic capable agent may occur by bulk degradation of the source. In another embodiment, the releasing the therapeutic capable agent may occur by diffusion through the source. In an embodiment, a device including a source of therapeutic capable agent and incorporating any one or more features of the present invention is delivered to a corporeal site, such as an intracorporeal body (e.g., body lumen). The corporeal site may be a targeted corporeal site (such as a targeted intracorporeal site), which includes the susceptible tissue site, or a targeted site directly or indirectly providing the therapeutic capable agent to the susceptible tissue site. The therapeutic capable agent is made available to the susceptible tissue site, preferably, in a controlled manner over a period of time.

Methods of treatment generally include positioning the source including the at least one therapeutic capable agent and/or optional another compound within the intracorporeal body, concurrently with or subsequent to, an interventional treatment. More specifically, the therapeutic capable agent may be delivered to a targeted corporeal site (e.g., targeted intracorporeal site) which includes the susceptible tissue site or a targeted site providing the therapeutic capable agent to the susceptible tissue site, concurrently with or subsequent to the interventional treatment. By way of example, following the dilation of the stenotic region with a dilatation balloon, a device (such as a stent) according to the present invention, is delivered and implanted in the vessel. The therapeutic capable agent may be made available to the susceptible tissue site at amounts which may be sustainable, intermittent, or continuous; at one or more phases; and/or rates of delivery.

In an embodiment, the release of the therapeutic capable agent to the susceptible tissue site may be delayed. During the delay period none to small amounts of therapeutic capable agent may be released before the release of a substantial amount of therapeutic capable agent. Typically, the delay is sufficiently long to allow for sufficient generation of intimal tissue or cellularization at the treated site to reduce the occurrence of a thrombotic event.

In an embodiment, the method further includes directing energy at the device to effect release of the therapeutic capable agent from the device. The energy may include one or more of ultrasound, magnetic resonance imaging, magnetic field, radio frequency, temperature change, electromagnetic, x-ray, heat, vibration, gamma radiation, or microwave.

BRIEF DESCRIPTION OF THE DRAWINGS

FIGS. 2A and 2B are high magnification images of a drug eluting stent according to the present invention having a textured surface.

FIGS. 3A and 3B are high magnification images of a drug eluting stent having a smooth surface.

FIGS. 9A and 9B are schematic representations of spray apparatus and methods for making the stent of FIG. 4A.

FIGS. 10A and 10B are schematic representations of a method for crimping the stent of FIG. 4A onto a balloon catheter.

DETAILED DESCRIPTION OF THE INVENTION

Figure 1A:
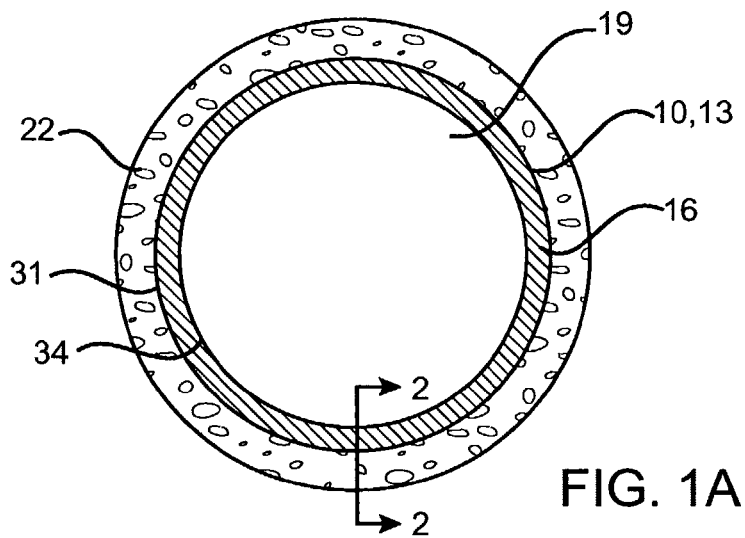
FIGS. 1A through 1C are cross-sectional views of a device embodying features of the present invention and implanted in a body lumen.
Figure 1B:
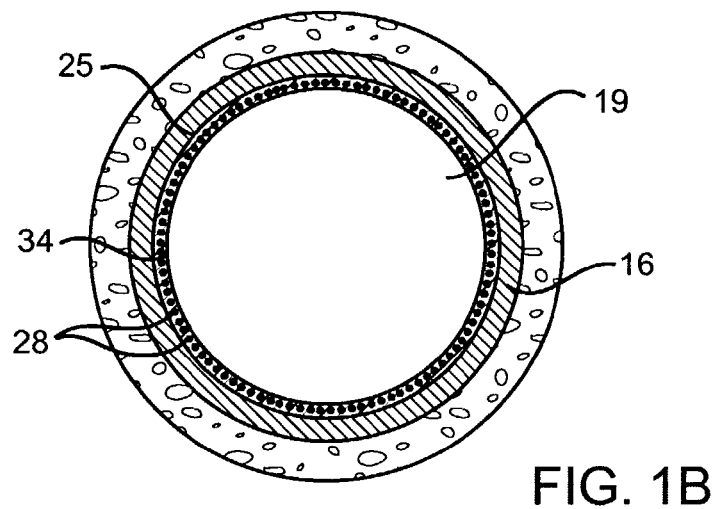
Figure 1C:
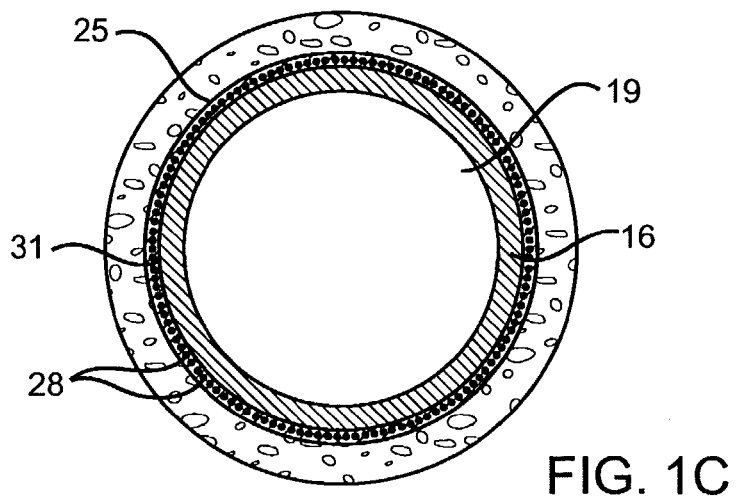

FIGS. 1A–1C, illustrate a device 10, such as a prosthesis 13, embodying features of the invention and generally including an expandable structure 16 implantable in an intracorporeal body, such as body lumen 19 including a susceptible tissue site 22, and a source 25 adjacent the expandable structure 16 including a therapeutic capable agent 28. The device 10, as shown, is disposed in the body lumen 19. It should be appreciated, that although the source 25 as depicted in the figures is disposed adjacent a surface of the expandable structure, the term "adjacent" is not intended to be limited by the exemplary figures or descriptions.

The expandable structure 16, as shown without intending any limitation, has a tissue facing (abluminal) surface 31 and a luminal facing surface 34, and optionally an interior 37 which may include a lumen. It will be appreciated that the following depictions are for illustration purposes only and do not necessarily reflect the actual shape, size, configuration, or distribution of the prosthesis 13. The prosthesis may have a continuous structure or an intermittent structure as the case may be with many stents (e.g., a cross section of a stent does not entirely include a substrate forming the expandable structure, for example, some stents have a screen or mesh like cross section). The source may be disposed or formed adjacent at least a portion of either or both the luminal surface, as shown in FIG. 1B, the abluminal surface, as shown in FIG. 1C, within the interior of the expandable structure, and/or or any combination thereof.

The source may comprise one or a plurality of compounds, as for example the first therapeutic capable agent 28 and an optional another compound, such as an another or second therapeutic capable agent. Each of the plurality of compounds may be in the same or different area of the source.

FIGS. 2A and 2B generally show a portion of a surface of an expanded therapeutic capable agent eluting stent 40 embodying features of the present invention at different magnifications and having a therapeutic capable agent source 43. As can be seen from these figures, the therapeutic capable agent layer 46 has a textured surface. The therapeutic capable agent source surface is substantially continuous and free from dislodged therapeutic capable agent portions. As used herein, "continuous" refers to a surface that has at least a substantially continuous surface without substantive dislodged portions. The surface of the therapeutic capable agent layer is such that it does not expose, at least not substantially, the underlying structure surface.

By way of comparison, FIGS. 3A and 3B generally show a portion of a surface of an expanded therapeutic capable agent eluting stent 50 at different magnifications and having a therapeutic capable agent source 53. As can be seen from these figures, the therapeutic capable agent layer 56 has a relatively smooth surface in the non-dislodged areas 59. However, the therapeutic capable agent layers includes surface defects, by way dislodged portions 62, in which the covering therapeutic capable agent layer is lost exposing the underlying structure 16. Such defects may arise as a result of the stress created when the structure is expanded, as for example, within the intracorporeal lumen.

The therapeutic capable agent surface is preferably prepared to include a surface having peaks with a mean distance between adjacent peaks ranging from about 0.1 µm to about 50 µm, usually ranging from about 1 µm to about 35 µm, typically ranging from about 5 µm to about 20 µm. The peaks may have an average height (distance between the base of the peak and the apex of the peak) ranging from about 0.01 µm to about 10 µm, usually ranging from about 0.05 µm to about 1.5 µm, typically ranging from about 0.1 µm to about 1 µm. The therapeutic capable agent may be disposed to have an average thickness ranging from about 0.1 µm to about 20 µm, usually ranging from about 0.5 µm to about 7.5 µm, typically ranging from about 1 µm to about 5 µm.

The dimensions of the expandable structure will depend on its intended use. Typically, the expandable structure will have a length in a range from about 5 mm to about 100 mm, usually being from about 8 mm to about 50 mm, for vascular applications. The diameter of a cylindrically shaped expandable structure for vascular applications, in a non-expanded configuration, usually ranges from about 0.5 mm to about 10 mm, more usually from about 0.8 mm to about 8 mm; with the diameter in an expanded configuration ranging from about 1.0 mm to about 100 mm, preferably from about 2.0 mm to about 30 mm. The expandable structure usually will have a thickness in a range from about 0.025 mm to 2.0 mm, preferably from about 0.05 mm to about 0.5 mm.

Figure 4:
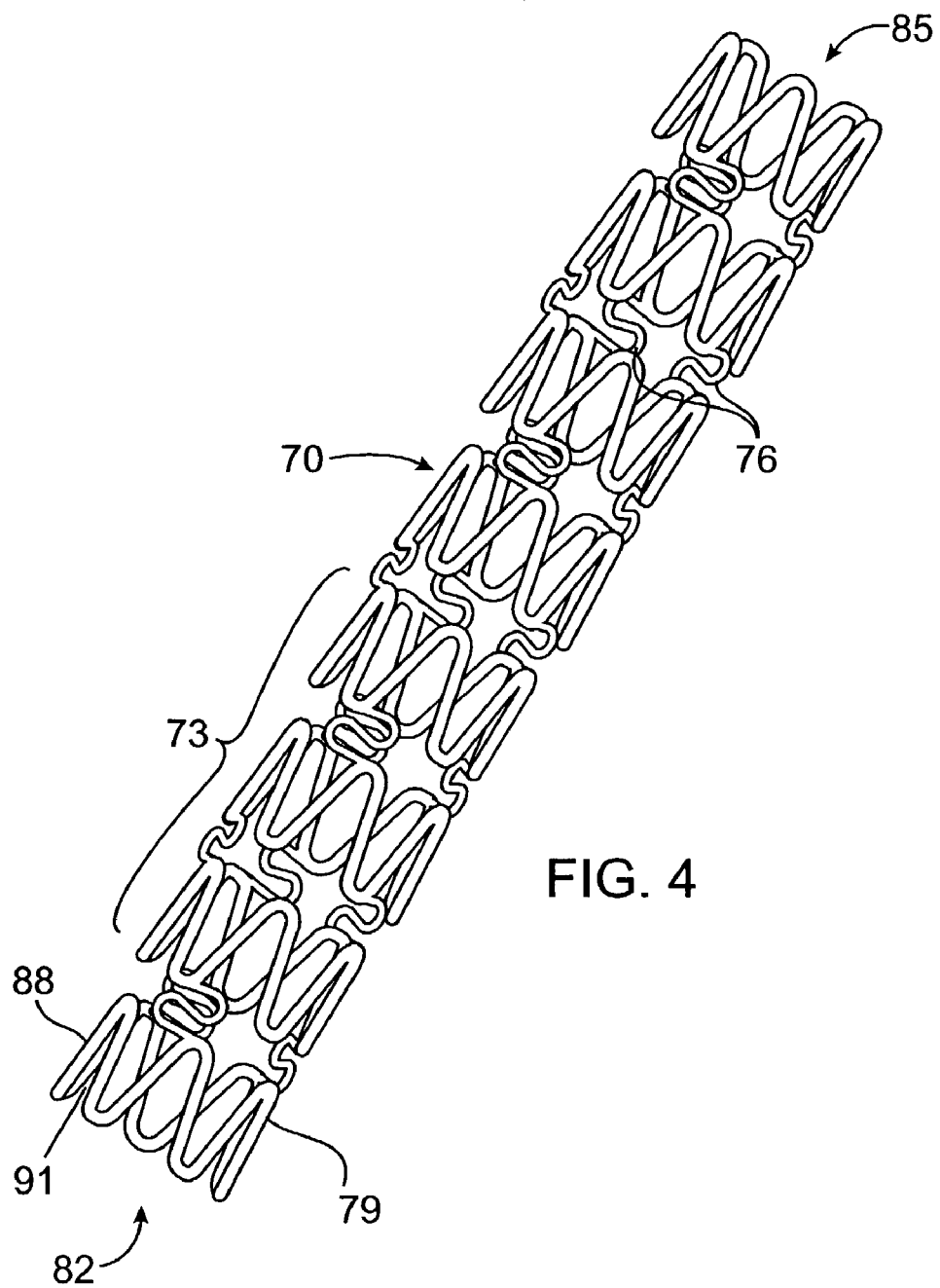
FIG. 4 is a schematic representation of an exemplary stent for use as the device of the present invention.

Now referring to FIG. 4, the expandable structure 16 may be a stent 70 or a graft (not shown). When the expandable structure is a stent, the expandable structure 16 will usually comprise at least two radially expandable, usually cylindrical, ring segments 73. Typically, the expandable structure 16 will have at least four, and often five, six, seven, eight, ten, or more ring segments. At least some of the ring segments will be adjacent to each other but others may be separated by other non-ring structures. The description of exemplary stent structures is not intended to be exhaustive and it should be appreciated that other variations of stent designs may be used in the present invention.

The exemplary stent 70 (embodying features of a stent described in more detail in co-pending U.S. patent application Ser. No. 08/968,319) for use in the present invention comprises from 4 to 50 ring segments 73 (with eight being illustrated). Each ring segment 73 is joined to the adjacent ring segment by at least one of sigmoidal links 76 (with three being illustrated). Each ring segment 73 includes a plurality of strut/hinge units, e.g., six strut/hinge units, and three out of each six hinge/strut structures on each ring segment 73 will be joined by the sigmoidal links 76 to the adjacent ring segment. As shown in FIG. 4, the stent 70 is in a collapsed or non-expanded configuration.

As used herein, the term "radially expandable" includes segments that can be converted from a small diameter configuration to a radially expanded, usually cylindrical, configuration which is achieved when the expandable structure 16 is implanted at a desired target site. The expandable structure 16 may be minimally resilient, e.g., malleable, thus requiring the application of an internal force to expand and set it at the target site. Typically, the expansive force can be provided by a balloon, such as the balloon of an angioplasty catheter for vascular procedures. The expandable structure 16 preferably provides sigmoidal links between successive unit segments to enhance flexibility and crimpability of the stent.

Alternatively, the expandable structure 16 can be self-expanding. Self-expanding structures are provided by utilizing a resilient material, such as a tempered stainless steel, or a superelastic alloy such as a nitinol alloy, and forming the body segment so that it possesses a desired radially-expanded diameter when it is unconstrained, i.e. released from the radially constraining forces of a sheath. In order to remain anchored in the body lumen, the expandable structure 16 will remain partially constrained by the lumen. The self-expanding expandable structure 16 can be tracked and delivered in its radially constrained configuration, e.g., by placing the expandable structure 16 within a delivery sheath or tube and removing the sheath at the target site.

Figure 4A:
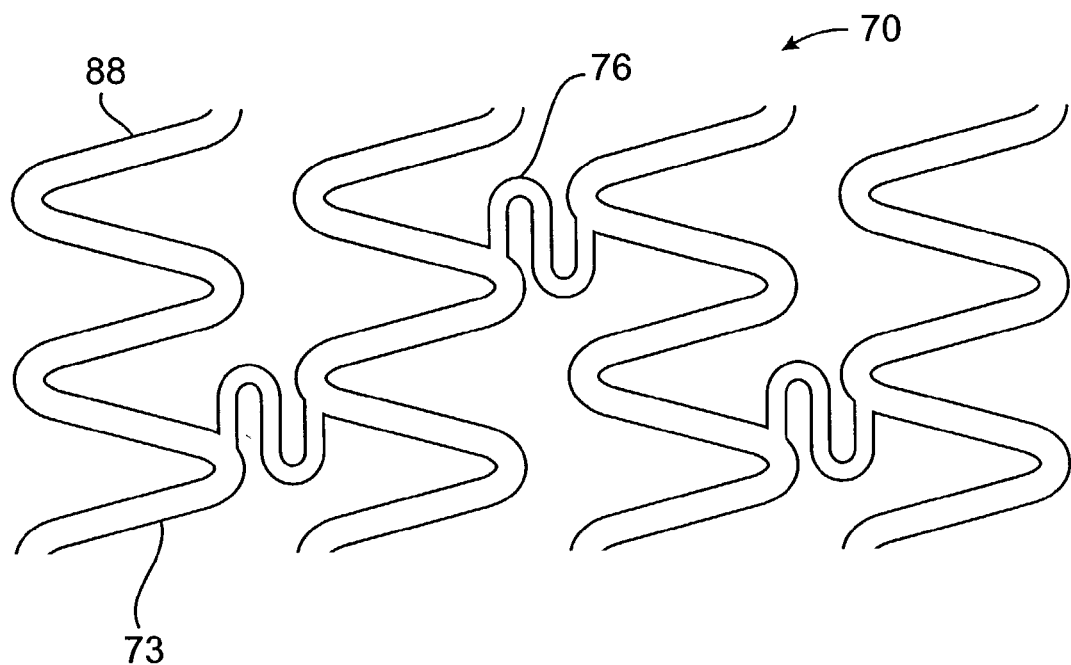
FIGS. 4A and 4B are schematic representations of an expanded view of a portion of the stent of FIG. 4 showing areas having different mechanical profiles.
Figure 4B:
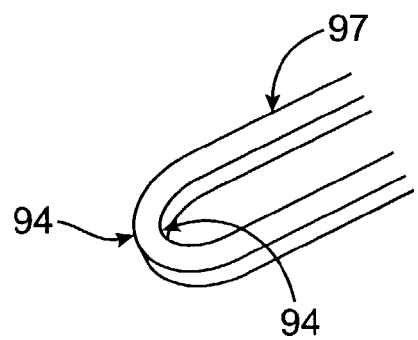

Now referring back to FIGS. 4A and 4B, the exemplary stent 70 generally includes a cylindrical frame 79 having proximal and distal ends, 82 and 85, abluminal and luminal facing surfaces, 88 and 91, a plurality of radially expansible unit segments including rings 73. The unit segments generally include segments having different mechanical profiles which, for example, may be exhibited as a result of expansion. For example, the segments may include relatively higher mechanical profile portions 94 at bends, points, intersections, joints, or areas exposed to flow turbulence and relatively lower mechanical profile portions 97 along their lengths. The areas exhibiting relatively lower mechanical profiles 97, upon the expansion of the stent, typically do not cause flaking and/or premature loss of the therapeutical agent under substantial bending, flexing, stretching, or compression, usually being less than about 5%. Some of the rings 73, as shown, are joined with at least one axially adjacent ring through expansion links 76, preferably having a sigmoidal shape, more preferably, an S shape having a relatively smooth profile along its length to minimize or reduce kinking upon expansion. Preferably, the rings 73, as shown, have a serpentine shape. Similarly, the links may comprise segments having different mechanical profile profiles along their length. For example, the unit segments and/or links may include relatively lower mechanical profile portions along their lengths with relatively higher mechanical profile portions at bends, points, intersections, joints, or areas exposed to flow turbulence (i.e., areas which are substantially in the direct line of fluid (e.g., blood or other bodily fluids) flow through the body).

Figure 5A:
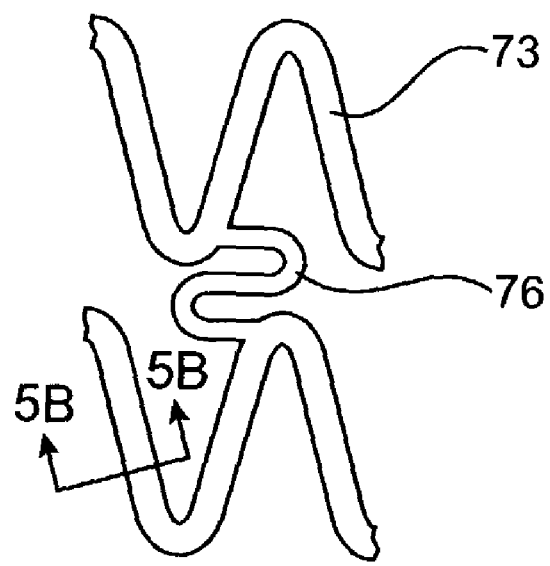
FIGS. 5A through and 6H are schematic representations of different embodiments of the stent of FIG. 4A.
Figure 5B:
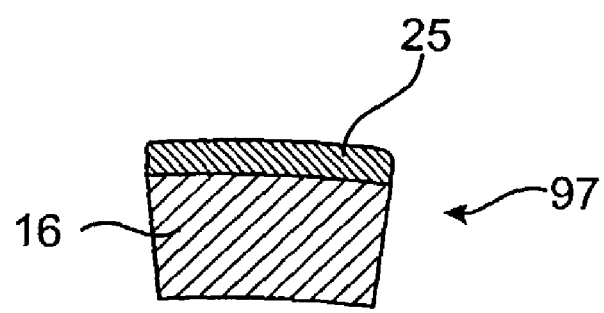
Figure 6B:
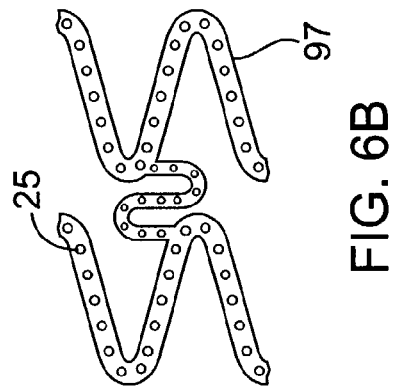
Figure 6D:
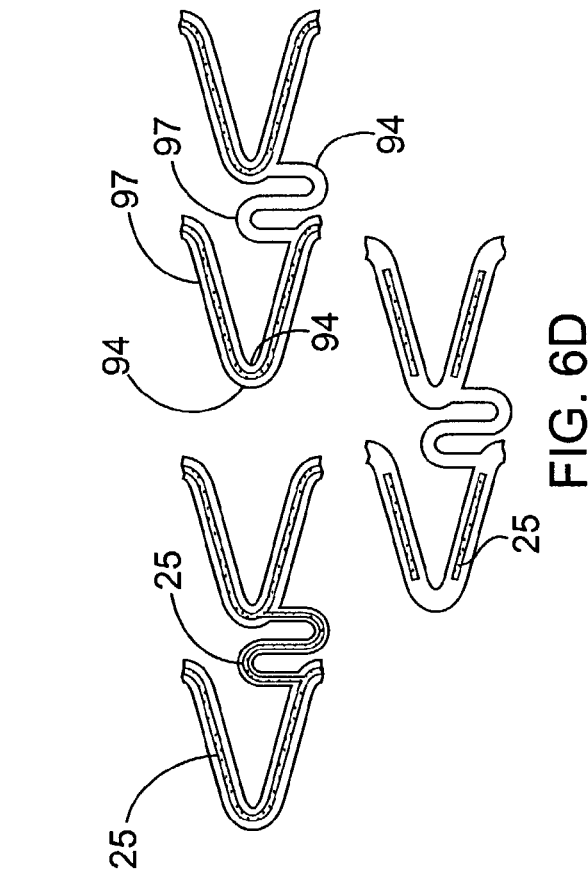
Figure 6A:
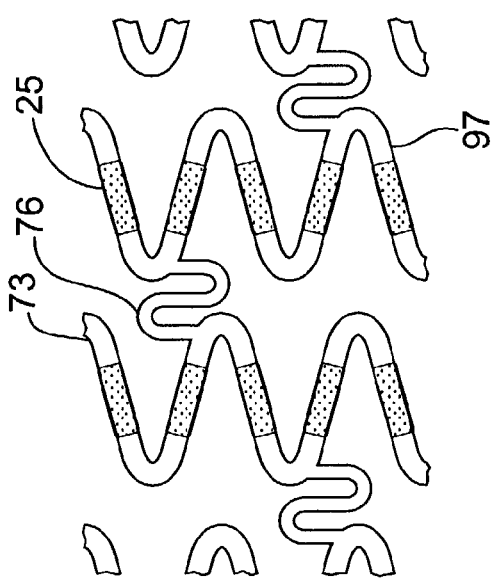
Figure 6C:
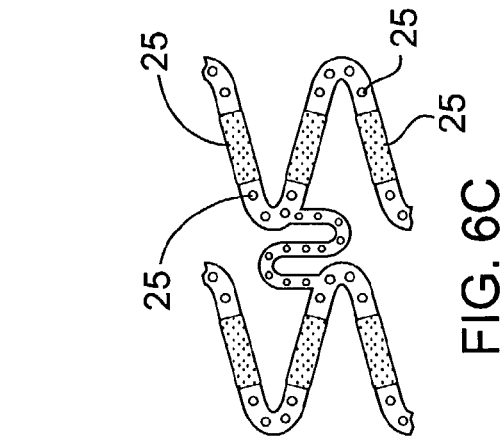
Figure 6E:
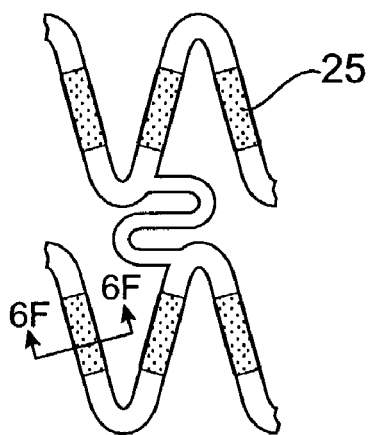
Figure 6F:
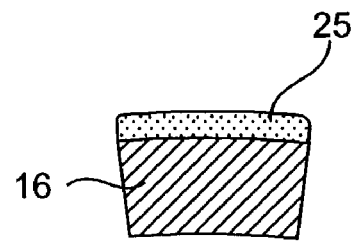
Figure 6G:
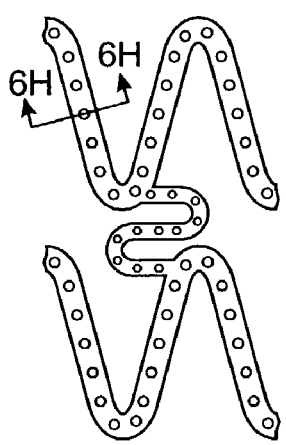
Figure 6H:
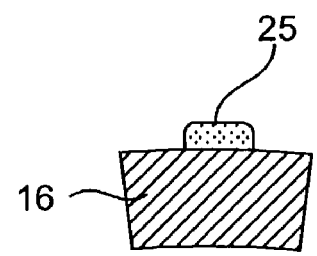

In an embodiment, as shown in FIGS. 5A and 5B, the therapeutic capable agent is disposed adjacent all of the surface of at least one of the abluminal and luminal surfaces of the structure, on both the higher and lower stress areas, 94 and 97. As shown in FIGS. 6A through 6H, the source may be disposed on all of at least one of the abluminal or luminal surfaces or only on the portions of the cylindrical frame, usually, only on those portions of the ring and/or links, 73 and 76, having relatively lower mechanical profiles 97. The therapeutic capable agent may be applied in discrete portions, the portions having relatively larger areas (e.g., FIGS. 6A, 6E, and 6F), preferably on areas having relatively lower mechanical profiles. Alternatively or additionally, the therapeutic capable agent may be present in smaller surface areas (e.g., FIGS. 6B and 6C), preferably along the outer surfaces of the structure and away from sides and/or edges of the rings and/or the links (e.g., FIGS. 6D, 6G, and 6H).

The source may vary in the amount of the therapeutic capable agent it comprises. When the source is present in a plurality of segments, as for example, when present in discrete portions, each source may comprise same or different therapeutic capable agents, at same or different amounts, and may make the therapeutic capable agent available to the susceptible tissue site at same or different phases and/or rates. The source may be present as a single layer, or a plurality of layers immediately adjacent one another or separated by another layer (e.g. a third layer).

In one embodiment, the device may include areas (e.g., radial distal and proximal ends of the device) having variable thickness of the source to allow for slower or faster release rates.

In yet another embodiment, the therapeutic capable agent has a degree of crystallinity less than about 90%, sometimes less than about 50%. Lower crystallinity may be achieved by heating any of the embodiments of the therapeutic capable agent eluting device to a higher temperature, usually about or greater than a melting point of the therapeutic capable agent, for a period of time sufficient to bring about the desired degree of crystallinity, usually from about 1 minute to about 24 hours, typically from about 30 minutes to about 2 hours. As the therapeutic capable agent melts, it becomes more amorphous and thus less brittle. The amorphous (or semi-amorphous) nature of the therapeutic capable agent provides for a more controlled rate of release. The heating of the therapeutic capable agent-coated device may additionally serve to change, as for example, reduce the residual stress of the device due to the molecular re-arrangement of the therapeutic capable agent.

The residual stress of the coated device due to the therapeutic capable agent may be also reduced by other means, such as, heating the device to a temperature below the melting point of the therapeutic capable agent, heating for a longer period of time, and using other sources of energy including ultrasonic, magnetic, or vibrational energies.

The expandable structure may include the therapeutic capable agent, by coating, spraying, dipping, deposition (vapor or plasma), or painting the therapeutic capable agent onto the prosthesis. Usually, the therapeutic capable agent is dissolved in a solvent prior to its application. Suitable solvents include aqueous solvents (e.g., water with pH buffers, pH adjusters, organic salts, and inorganic salts), alcohols (e.g., methanol, ethanol, propanol, isopropanol, hexanol, and glycols), nitrites (e.g., acetonitrile, benzonitrile, and butyronitrile), amides (e.g., formamide and N-dimethylformamide), ketones, esters, ethers, DMSO, gases (e.g., $CO_2$), and the like. The therapeutic capable agent-structure is then allowed to dry. Alternatively, the therapeutic capable agent may first be prepared into a matrix by mixing or dissolving the therapeutic capable agent and matrix material, alone or in combination with a solvent, prior to its incorporation to the structure.

In an exemplary method of making the devices of the present invention, a bare or uncoated stent is first fabricated and/or processed (e.g., descaled, electropolished, passivated) using conventional methods prior to the including of the therapeutic capable agent. By way of example, the bare stent is optionally treated with coupling agents such as silane, plasma deposited coating, plasma treatment, coronary discharge, descaleing, passivation, and/or other means to promote and/or enhance the adhesion of the therapeutic capable agent to the bare stent in subsequent steps.

Figure 7A:
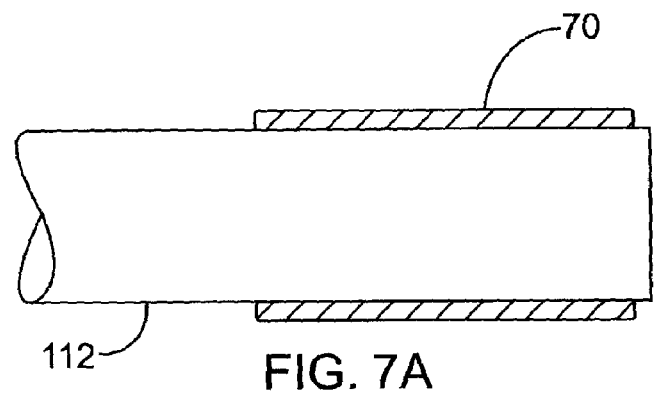
FIGS. 7A through 7D are schematic representations of different embodiments of apparatus and methods for making the stent of FIG. 4A.

In an exemplary method of making the therapeutic capable agent eluting stents of the present invention, the therapeutic capable agent of choice is prepared as a solution (e.g., using ethanol as the solvent) at a desired concentration. A spray valve reservoir of a sprayer, such as EFD 780S Series Spray available from EFD Corporation (Providence, R.I.), is filled with the therapeutic capable agent solution. A stent, such as Duraflex™ stent available form Avantec Vascular Corporation, Sunnyvale, Calif., is provided and weighed to measure its initial uncoated weight. As shown in FIG. 7A, a mandrel 112 having an outer diameter, preferably, similar to that of the inner diameter of the stent, is positioned within the frame of the stent. To better maintain the stent onto the mandrel, the stent may be sufficiently crimped onto the mandrel so as to prevent the stent from slipping off the mandrel. The stent is then loaded onto a rotating fixture disposed under the nozzle head. The therapeutic capable agent solution is then applied to the stent as the nozzle head traverses along the length of the stent while the stent rotates radially. This process is continued until the desired amount of therapeutic capable agent has been applied to the stent. The stent is heated to remove the residual solvent, as for example, by being placed in a vacuum, oven, or vacuum oven. The stent may then be weighed to measure and calculate the amount of therapeutic capable agent applied to the stent.

The mandrel, when formed of a solid material or one having a closed exterior surface, may optionally serve as a mask to shield the inner surface of the cylindrical frame (i.e., the luminal surface of the stent) during coating steps to make a device wherein the therapeutic capable agent is at least substantially being disposed adjacent the abluminal surface of the device. Optionally, a mandrel having an outer diameter sufficiently smaller than the inner diameter of the stent and/or one being formed of a sufficiently open lattice structure (the pattern preferably designed to prepare the desired coating pattern on the stent), may be used to allow for the coating of the luminal surface of the stent during the coating process.

Figure 7B:
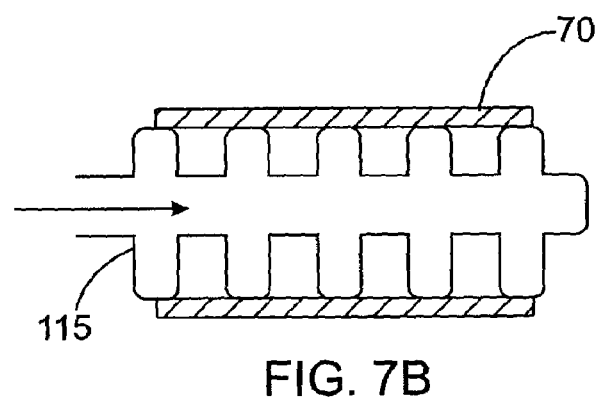

Optionally, an expansible balloon 115 having a generally cylindrical expanded shape and formed, preferably, from a material such as silicone rubber, polyurethane, nylon, or the like, may be used as the mandrel. The balloon in its expanded configuration, preferably, has an outer diameter, similar to that of the inner diameter of the stent. Use of the balloon as the mandrel allows for easier removal from the stent after completion of the coating process. As shown in FIG. 7B, the balloon may be formed so as to include a series of longitudinally spaced apart areas of larger diameter (such as a centipede shape). The larger diameter areas are sufficiently spaced apart so as to come in contact with the luminal surface of the stent being of relatively higher mechanical profile, thus masking the relatively higher stress areas during the coating process. In yet another optional embodiment, the balloon comprises an exterior tubing formed from a soft material such as soft rubber such that the balloon can be positioned in the spaces between the rings and/or links to mask the edges of the same, thus, allowing coating only on the abluminal surface of the stent while masking the edges (e.g., thickness) of the rings and/or links.

Figure 7C:
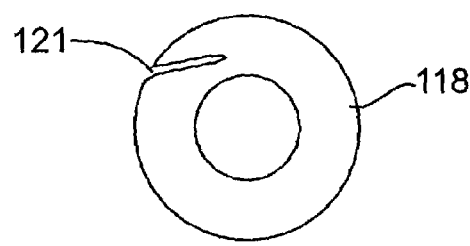
Figure 7D:
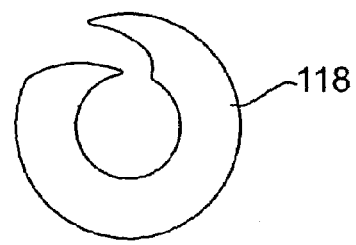

In yet another embodiment of a process of making the devices of the present invention, to avoid or minimize the coating of the stent at the relatively higher mechanical profile areas, one or more washers 118 shown in FIGS. 7C and 7D, such as silicone rubber washers (or of other materials/shapes as may be desired), are disposed over the relatively higher mechanical profile areas of the tissue facing surface of the stent, thus masking these areas during the coating process. After the application of the drug, the washer, such as that depicted in FIG. 7C, may be torn across a tear 121 to allow for easy removal from the device. The washers may have an inner diameter substantially the same, slightly larger, or more preferably, smaller than the inner diameter of the stent. Preferably, the washers have a width greater than the width of the relatively higher mechanical profile areas of the stent.

In yet another embodiment, the structure may be masked by creating a negative image of the structure on another material, such as a plastic or metal tube. The tube can be slitted into two halves. The slitted tube is then clamped onto the stent. Only the outer surface of the stent is exposed. The stent sides and luminal surface are not exposed. When the therapeutic capable agent is sprayed onto the stent, the therapeutic capable agent is only on the outer surface of the stent. This would result in FIGS. 6B, 6D, 6G, or similar embodiments.

Figure 8A:
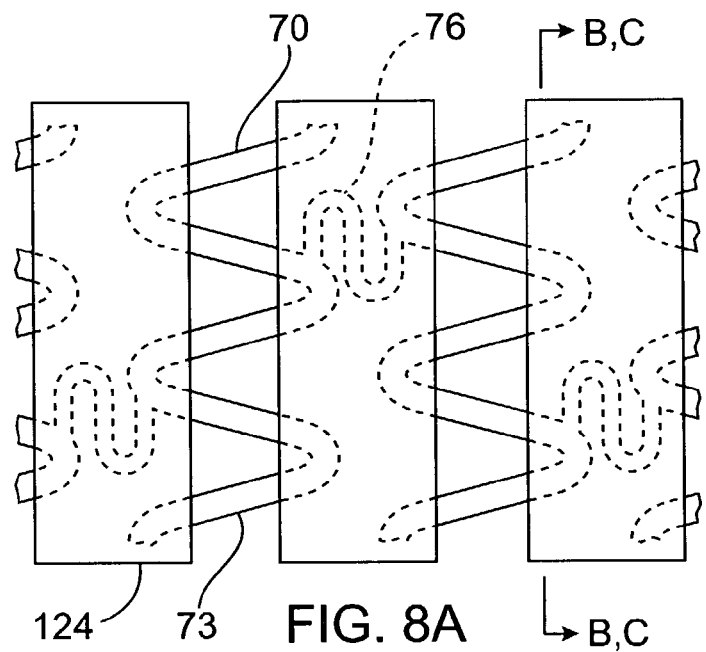
FIGS. 8A through 8C are schematic representations of another embodiment of masking apparatus and methods for making the stent of FIG. 4A.
Figure 8B:
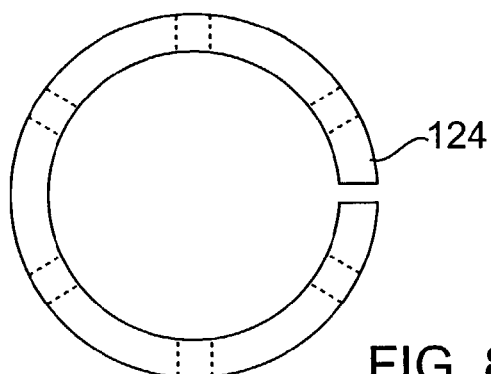
Figure 8C:
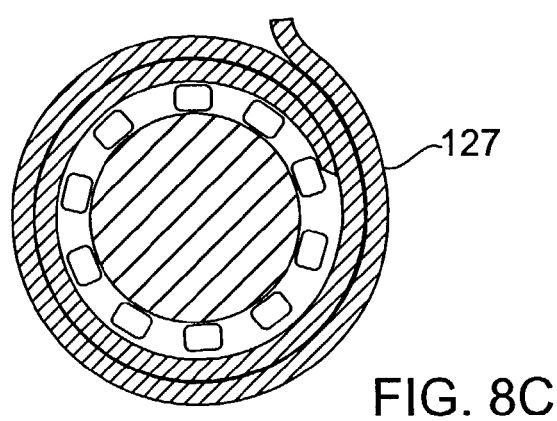
Figure 11A:
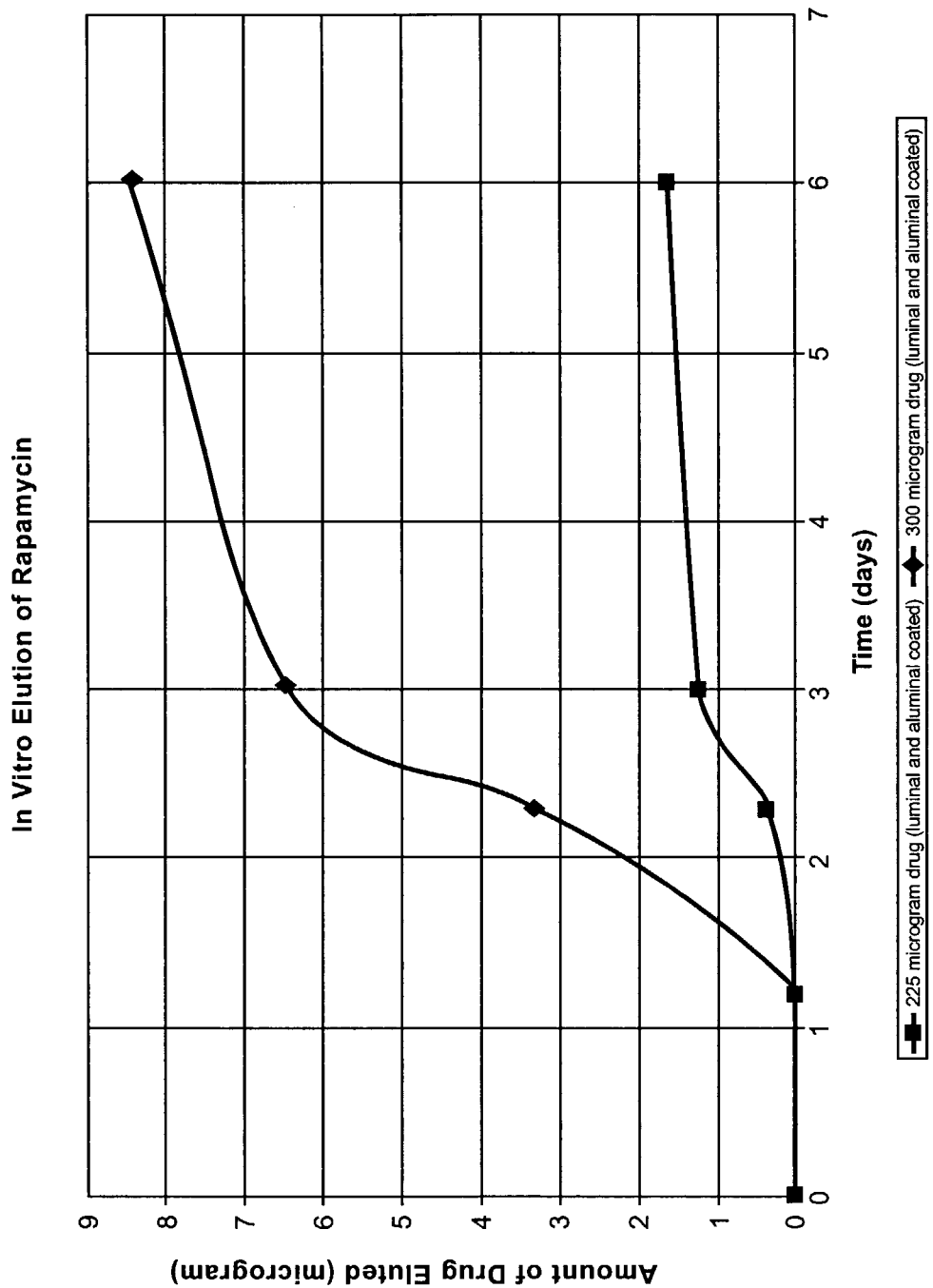
FIGS. 11A through 11D are graphical representations of the release of different therapeutic capable agents over time according to the present invention.
Figure 11B:
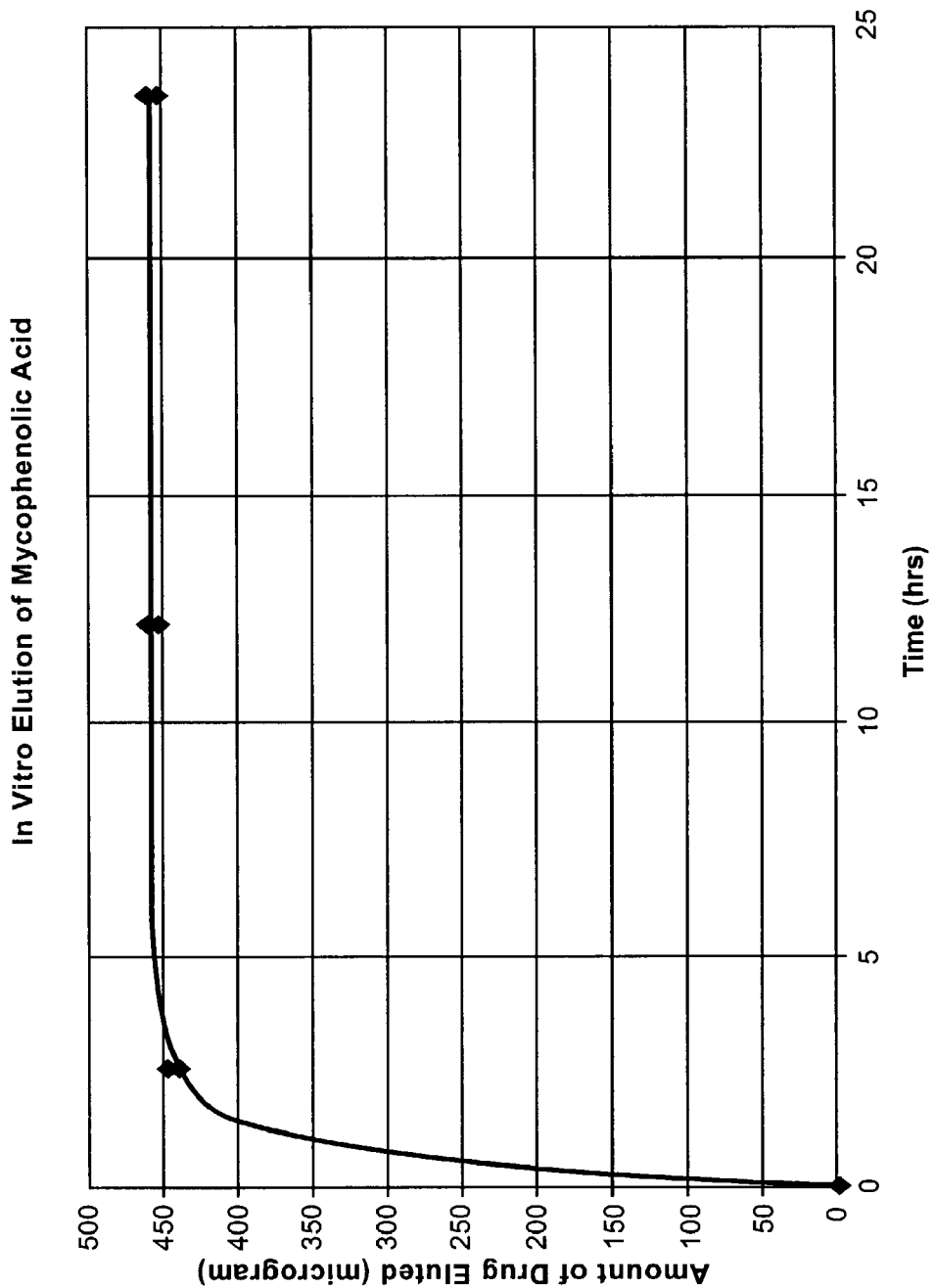
Figure 11C:
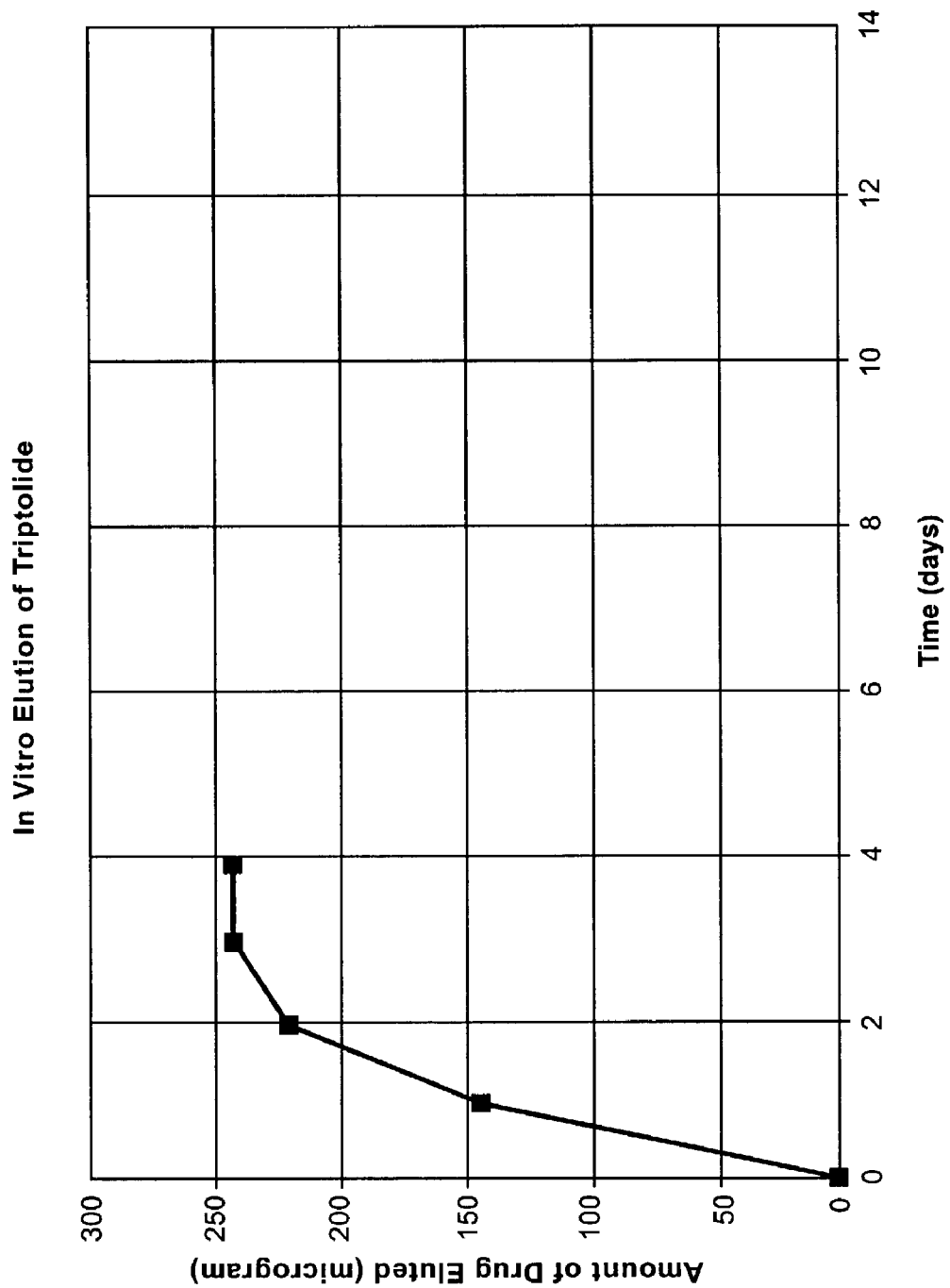
Figure 11D:
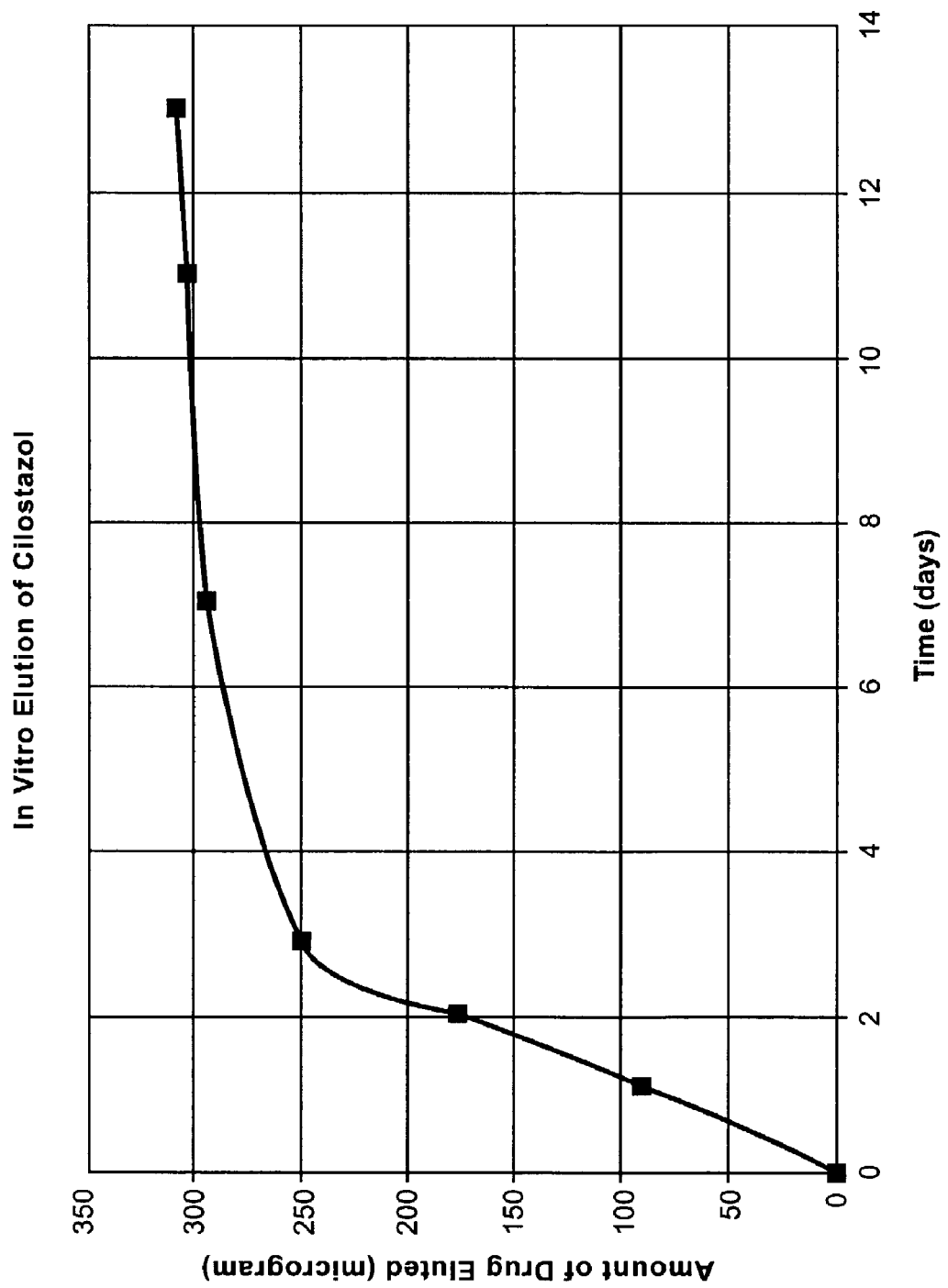

To mask desired portions, such as structure areas having a relatively higher mechanical profile, the stent structure may be masked, as shown in FIG. 8A, by a variety of ways such as a flat plate, curve plate, a tube, or other surfaces 124 having exposed apertures or slots. As seen in FIG. 8B, the aperture and/or slots expose the desired areas to coating (e.g., low mechanical profile areas) while masking the other areas (e.g., high mechanical profile areas). Alternatively, a flexible tape 127, as shown in FIG. 8C, may be used to cover the tissue facing surface of the stent at the high mechanical stress areas.

In another embodiment, the stent is either not masked or is minimally masked during the coating. If desired, unwanted areas of coating may be removed by way of application of fine tip sand blaster, high pressure air nozzle, high pressure spray nozzle with an appropriate solvent (e.g., methanol, ethanol, isopropanol acetone, water), low power laser, electron beam, or the like. Alternatively, a very fine spray nozzle or nano-size deposition tool may be used to selectively apply the therapeutic capable agent to or onto the structure.

The stent, masked or unmasked, is then exposed to a source of therapeutic capable agent, as shown in FIGS. 9A and 9B. The therapeutic capable agent 28 is preferably dissolved or mixed in an appropriate solvent(s) and/or matrix material and applied by methods such as spraying. Preferably, the stent is removably fixed to a rotating device so that the stent may be evenly disposed with the source (i.e., therapeutic capable agent as dissolved in a solvent and/or matrix material). Preferably, the width of the source application device is sufficiently long so as to apply the source onto the entire length of the stent.

Alternatively, the stent may be coated with the source using other techniques, such as, powder coating while the stent is in a vacuum deposition chamber or plasma deposition/glow discharge chamber, pulse laser assisted deposition technique, vacuum deposition with the therapeutic capable agent being vaporized in the high vacuum chamber and thereafter deposited onto the stent. After the completion of the coating, the masks are removed from the stent. Excess therapeutic capable agent, if necessary or desired, may be removed from the coated stent as described earlier.

The characteristics of the therapeutic capable agent layer, such as thickness and surface characteristics, may be controlled by a variety of factors including any one or more of the following: therapeutic capable agent solution concentration, coating solution droplet size (as may be controlled in one way by the coater nozzle size), the rate of therapeutic capable agent coating (μg/second), the speed of rotation of the mandrel, the speed of the nozzle movement along the length of the stent, the number of traverse passes of the sprayer along the length of the stent, the length of time elapsed between each pass for any given point along the length of the stent, direction of traverse passes (e.g., always from one end to the other or a wrap-around technique (e.g., traversing from proximal to distal end in first pass and then from distal to proximal end in the second pass)), time between the coating, the width of the sprayer nozzle, the of the duration of coating process.

Therapeutic capable agent eluting stents lacking a protective coating or matrix material may be difficult to crimp on a balloon catheter. Abrasion between a crimping device and the therapeutic capable agent layer on the stent may result in fracture of the therapeutic capable agent layer during the crimping of the stent from a larger diameter to a smaller diameter as well as during removal of the crimping device.

FIGS. 10A and 10B illustrate an exemplary method for crimping the therapeutic capable agent eluting stent 70 on a balloon catheter 129 with minimal damage to the therapeutic capable agent layer. A pipette 131 or taper tube with a 0.052" inner tip diameter is first slipped over the balloon PTA catheter 129. The stent is initially crimped by hand or mechanical means to a smaller diameter (e.g., from 0.066" outer diameter to 0.050" outer diameter). The amount of friction provided by this step is insignificant and does not result in fracturing of the therapeutic capable agent layer. A teflon sheath 133 or low coefficient of friction tubing with an inner diameter above 0.050" is slipped over the crimped stent. A distal end of the teflon sheath is beveled. With the teflon sheath 133 over the stent 70, the bevel end of the sheath is inserted into the pipette 131. The bevel end is then gripped (i.e., with a set of pliers), as depicted by arrow 135, while the pipette is pulled an entire length of the sheath. The teflon sheath can then be removed by pulling it out from the catheter. However, it is more preferable to split the teflon sheath (which is non-isotropic in nature) along its length so that there is minimal abrasion between the sheath and the therapeutic capable agent layer.

Normally, the therapeutic capable agent eluting device, such as a coronary stent, is selected to have a length at least equal to a length of an injured site (e.g., lesion) so as to extend the entire length of a lesion, preferably extending beyond the lesion. However, in some instances, stenosis is known to have been developed or increased at edges of the stent and/or beyond the stented or covered tissue area. This is known as "edge effect" or candy wrapper effect. In patients experiencing the edge effect, although the stented portion may remain free of significant restenosis, the site at or beyond the edges of the stent may develop significant or even severe stenosis, requiring subsequent treatment. The severity of the stenosis at the edge and/or beyond edge areas is usually greater at an area proximal to the stent as compared to an area distal to the stent. The occurrence of edge effect may be attributable to uncovered diseased segments subjected to balloon trauma that are not covered by the stent, migration of smooth cells from the lesioned area, injury during the interventional procedure (e.g., balloon injury during angioplasty with or without the stenting), or the insufficient coverage of the original lesion. In the case of drug eluting stents, such effect may further be attributable to drastic gradient change between areas directly exposed to the drug and areas not directly exposed to the drug.

In an embodiment, the devices and methods of the present invention inhibit hyperplasia and/or restenosis at a stented area (i.e., in stent restenosis or ISR) as well as at areas of the vessel at and/or beyond edges of the stent (i.e., peri-stent). The peri-stent area may include either or both areas longitudinally proximal and distal to the stent. Usually such peri-stent area has a longitudinal dimension of about five (5) millimeters on either end of the stent. The inhibition at the proximal peri-stent area may be the same, less, or greater than that at the distal peri-stent area. The present devices provide a higher level of therapeutic capable agent to the peri-stent area, as compared to devices where the release of the therapeutic capable agent is limited by the presence of rate controlling elements in the form of a therapeutic capable agent/polymer matrix or as in the form of a polymer layer disposed adjacent and over the therapeutic capable agent.

EXAMPLES

Example 1

Preparation of a drug eluting stent according to the present invention. A drug solution at a concentration of 0.030 gram benidipine per ml of Ethanol was prepared. A spray valve reservoir was filled with the drug solution using an EFD 780S Series spray valve with a 0.028" diameter spray nozzle head (part number 7857-28SS). An 18 mm Duraflex™ stent was provided and weighed (initial weight). A 0.014" U-shaped wire mandrel was inserted inside the stent. The stent was fixed to a rotating fixture located at about 0.5 inches under the nozzle head. The stent was sprayed with the drug solution with a stroke control knob of the spray valve set at 0.75, reservoir pressure of 12 psi, and nozzle air pressure of 25 psi. While the spray valve was moved horizontally across the length of the stent, the drug solution was sprayed on the surface of the stent. The stent was coated until the desired amount of drug (e.g., 300 µg) was deposited on the stent. The mandrel was removed from the stent and the stent was let dry in a vacuum oven at about 85° C. for about one (1) hour to remove the solvent. The stent was weighed again (final weight) and the weight of the drug present on the stent was calculated by subtracting the initial weight of the stent from the final weight of the stent. As seen in FIGS. 2A and 2B, the drug coated stent in an unexpanded state had a texture drug coating layer.

A second drug eluting stent was prepared by applying a drug solution at a concentration of 0.020 mg/ml as described above in this example with the exception that the stroke control knob setting was lowered from 0.75 to 0.5. Upon visual inspection the first and second drug eluting stents had similar surface characteristics.

Example 2

Preparation of a drug eluting stent having smooth drug coating layer. A drug solution at a concentration of 0.030 g of benidipine per ml of Ethanol was prepared. A spray valve reservoir was filled with the drug solution using an EFD 780S Series spray valve with a 0.028" diameter spray nozzle head (part number 7857-28SS). An 18 mm Duraflex™ stent was provided and weighed (initial weight). A 0.014" U-shaped wire mandrel was inserted inside the stent. The stent was fixed to a rotating fixture located at about 0.5 inches under the nozzle head. The stent was sprayed with the drug solution with a stroke control knob of the spray valve set at 1, reservoir pressure of 12 psi, and nozzle air pressure of 25 psi. While the spray valve was moved horizontally across the length of the stent, the drug solution was sprayed on the surface of the stent until the desirable amount of drug (e.g., 300 µg) was deposited on the stent. The mandrel was removed from the stent and the stent was let dry in a vacuum oven at about 85° C. for about one (1) hour to remove the solvent. The stent was weighed again (final weight) and the weight of the drug present on the stent was calculated by subtracting the initial weight of the stent from the final weight of the stent. As can be seen from FIGS. 3A and 3B, the drug coated stent in an unexpanded state had a smooth drug coating layer.

A second drug eluting stent was prepared by applying a drug solution at a concentration of 0.020 mg/ml as described above in this example with the exception that the stroke control knob setting was lowered from 1 to 0.75. Upon visual inspection the first and second drug eluting stents had similar surface characteristics.

Example 3

In an effort to evaluate the effect of drug layer surface characteristics on drug loss from a drug eluting stent upon expansion, two groups of stents with two stents in each group, were prepared to include a different drug layer, mycophenolic acid and benidipine, respectively. Within each group, a drug solution was applied to 18 mm length stents according to the procedures described above in reference to Examples 1 and 2. In the case of the mycophenolic acid stents, about 300 µg of the drug solutions was applied in the form of a solution at a concentration of 0.010 mg/ml with a stroke control knob setting being set at 1.0 and 1.5, respectively, to obtain textured and smooth drug coating layers.

Each of the drug eluting stents was then expanded with a 3.0 mm×18 mm balloon. The balloon was then removed from the stent, the stent was weighed (expanded weight), and the weight of drug loss due to expansion (weight before expansion (e.g., final weight) minus the weight after expansion (e.g., expanded weight)) was calculated. As can be seen from the data in Table I below, the stent prepared according to the present invention having a textured surface had a lower amount of loss as compared to the stent prepared having a smooth surface.

TABLE I

| Stent | Weight of Drug on Stent Before Expansion (μg) | Weight of Drug on Stent After Expansion (μg) | Drug Loss Due to Expansion (μg) (% loss) |
|---|---|---|---|
| Stent with Smooth Drug Layer of benidipine | 300 | 282 | 13 (1.9%) |
| Stent with Textured Drug Layer of benidipine | 300 | 290 | 1 (1.1%) |
| Stent with Smooth Drug Layer of mycophenolic acid | 278 | 244 | 34 (12.2%) |
| Stent with Textured Drug Layer mycophenolic acid | 282 | 264 | 18 (6.4%) |

Example 4

In an effort to evaluate the effect of the location of the drug layer on drug loss from a drug eluting stent upon expansion, mycophenolic acid in the form of a solution at a concentration of 0.010 mg/ml was applied to two different 18 mm length stents as described in relation to Example 1 above. In the case of one stent, the stent was masked such that the areas exhibiting a relatively lower stress profile upon expansion were coated.

Each of the drug eluting stents was then expanded with a 3.0 mm×18 mm balloon. The balloon was then removed from the stent, the stent was weighed (expanded weight), and the weight of drug loss due to expansion (weight before expansion (e.g., final weight) minus weight after expansion (e.g., expanded weight)) was calculated. As can be seen from the data in Table II below, the stent prepared according to the present invention to have masked areas exhibited a lower amount of loss as compared to the stent prepared to have the drug coating on both the relatively higher and relatively lower stress profile areas.

TABLE II

| Stent | Weight of Drug on Stent Before Expansion (μg) | Weight of Drug on Stent After Expansion (μg) | Drug Loss Due to Expansion (μg) (% loss) |
|---|---|---|---|
| Masked | 560 | 560 | 0 (0%) |
| Not Masked | 540 | 514 | 26 (4.8%) |

Example 5

Drug elution stents were prepared according to Example 1 with the following therapeutic capable agents: rapamycin, mycophenolic acid, TRIPTOLIDE™, and cilostazol, at a total drug coating amount of 225 and 300 μg, 600 μg, 240 fig, and 300 μg, respectively. The drug coated stents were eluted in vitro, and the amount eluted was measured over a period of time, as shown in FIGS. 11A through 11D, respectively.

Although certain preferred embodiments and methods have been disclosed herein, it will be apparent from the foregoing disclosure to those skilled in the art that variations and modifications of such embodiments and methods may be made without departing from the true spirit and scope of the invention. Therefore, the above description should not be taken as limiting the scope of the invention which is defined by the appended claims.

What is claimed is:

1. A device for intracorporeal use, the device comprising:
   a structure; and
   at least one source of at least one therapeutic capable agent associated with the structure, the at least one therapeutic capable agent having a textured surface wherein the surface has peaks and valleys with a distance between the peaks ranging from about 5 μm to about 50 μm.

2. A device as in claim 1, wherein the distance between the peaks is a mean distance.

3. A device as in claim 1, wherein the surface has a peak height ranging from about 0.01 μm to about 10 μm.

4. A device as in claim 1, wherein the surface has a peak height ranging from about 0.05 μm to about 1.5 μm.

5. A device as in claim 1, wherein the surface has a peak height ranging from about 0.1 μm to about 1 μm.

6. A device as in claim 3, 4, or 5, wherein the peak height is an average peak height.

7. A device as in claim 1, wherein the therapeutic capable agent forms a layer having a thickness ranging from about 0.1 μm to about 20 μm.

8. A device as in claim 1, wherein the therapeutic capable agent forms a layer having a thickness ranging from about 0.5 μm to about 7.5 μm.

9. A device as in claim 1, wherein the therapeutic capable agent forms a layer having a thickness ranging from about 1.0 μm to about 5 μm.

10. A device as in claim 7, 8, or 9, wherein the layer thickness is an average thickness.

11. A device as in claim 1, wherein the textured therapeutic capable agent surface forms the outer most layer of the device.

12. A device as in claim 1, wherein the therapeutic capable agent is selected from the group consisting of immunosuppressants, anti-inflammatories, anti-proliferatives, anti-migratory agents, anti-fibrotic agents, proapoptotics, vasodilators, calcium channel blockers, anti-neoplastics, anti-cancer agents, antibodies, anti-thrombotic agents, anti-platelet agents, IIb/IIIa agents, antiviral agents, mTOR (mammalian target of rapamycin) inhibitors, non-immunosuppressant agents, and combinations thereof.

13. A device as in claim 1, wherein the therapeutic capable agent is selected from the group consisting of mycophenolic acid, mycophenolic acid derivatives (e.g., 2-methoxymethyl derivative and 2-methyl derivative), VX-148, VX-944, mycophenolate mofetil, mizoribine, methylprednisolone, dexamethasone, Certican (e.g., everolimus, RAD), rapamycin, ABT-773 (Abbot Labs), ABT-797 (Abbot Labs), TRIPTOLIDE, Methotrexate, phenylalkylamines (e.g., verapamil), benzothiazepines (e.g., diltiazem), 1,4-dihydropyridines (e.g., benidipine, nifedipine, nicarrdipine, isradipine, felodipine, amlodipine, nilvadipine, nisoldipine, manidipine, nitrendipine, barnidipine (Hypoca)), Ascomycin, Wortmannin, LY294002, Camptothecin, flavopiridol, isoquinoline, HA-1077 (1-(5-isoquinolinesulfonyl)-homopiperazine hydrochloride), TAS-301 (3-bis(4-methoxyphenyl)methylene-2-indolinone), Topotecan, hydroxyurea, Tacrolimus (FK 506), cyclophosphamide, cyclosporine, daclizumab, azathioprine, prednisone, diferuloymethane, diferuloylmethane, diferulylmethane, Gemcitabine, cilostazol (Pletal), tranilast, enalapril, quercetin, suramin, estradiol, cycloheximide, tiazofurin, zafurin, AP23573, rapamycin derivatives, non-immunosuppressive analogues of rapamycin (e.g., rapalog, AP2 1967, derivatives of rapalog), CCI-779 (an analogue of rapamycin available from Wyeth), sodium mycophernolic acid, benidipine hydrochloride, sirolimus, rapamine, metabolites, derivatives and combinations thereof.

14. A device as in claim 1, wherein the therapeutic capable agent is selected from the group consisting of mycophenolic acid, mycophenolate mofetil, rapamycin, Certican (everolimus, RAD), TRIPTOLIDE, benidipine, Tacrolimus (FK 506), cilostazol (Pletal), metabolites, derivatives and combinations thereof.

\* \* \* \* \*